United States Patent
Cini et al.

(10) Patent No.: US 12,134,635 B1
(45) Date of Patent: Nov. 5, 2024

(54) INTERLEUKIN 18 (IL-18) VARIANTS AND FUSION PROTEINS COMPRISING SAME

(71) Applicant: Sonnet BioTherapeutics, Inc., Princeton, NJ (US)

(72) Inventors: John K. Cini, Blairstown, NJ (US); Susan J. Dexter, Rye, NH (US)

(73) Assignee: Sonnet BioTherapeutics, Inc., Princeton, NJ (US)

( * ) Notice: Subject to any disclaimer, the term of this patent is extended or adjusted under 35 U.S.C. 154(b) by 0 days.

(21) Appl. No.: 18/740,390

(22) Filed: Jun. 11, 2024

Related U.S. Application Data

(60) Provisional application No. 63/658,322, filed on Jun. 10, 2024, provisional application No. 63/616,148, filed on Dec. 29, 2023.

(51) Int. Cl.
*C07K 14/54* (2006.01)
*C07K 16/18* (2006.01)
*C12N 15/64* (2006.01)

(52) U.S. Cl.
CPC .......... *C07K 14/54* (2013.01); *C07K 14/5434* (2013.01); *C07K 16/18* (2013.01); *C12N 15/64* (2013.01); *C07K 2317/622* (2013.01); *C07K 2319/00* (2013.01)

(58) Field of Classification Search
CPC .... C07K 14/54; C07K 14/5434; C12N 15/00; C12N 15/09
See application file for complete search history.

(56) References Cited

U.S. PATENT DOCUMENTS

| | | |
|---|---|---|
| 6,476,197 B1 | 11/2002 | Yamamoto et al. |
| 7,037,685 B2 | 5/2006 | Yamamoto et al. |
| 7,311,902 B2 | 12/2007 | Bam et al. |
| 7,736,636 B2 | 6/2010 | Mousa et al. |
| 7,875,709 B2 | 1/2011 | Dinarello et al. |
| 8,188,223 B2 | 5/2012 | Beirnaert et al. |
| 8,679,496 B2 | 3/2014 | Coulstock et al. |
| 8,921,528 B2 | 12/2014 | Holt et al. |
| 9,012,609 B2 | 4/2015 | Arulanantham et al. |
| 9,175,071 B2 | 11/2015 | De Angelis et al. |
| 9,321,832 B2 | 4/2016 | Tomlinson et al. |
| 9,790,475 B2 | 10/2017 | Buller et al. |
| 9,803,004 B2 | 10/2017 | Adams et al. |
| 9,897,077 B2 | 2/2018 | Chen et al. |
| 11,850,276 B2 | 12/2023 | Ring et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |
| 2014/0170109 A1 | 6/2014 | Wulhfard |
| 2014/0341885 A1 | 11/2014 | Diluzio et al. |
| 2015/0307629 A1 | 10/2015 | Bernett et al. |
| 2016/0215063 A1 | 7/2016 | Bernett et al. |
| 2017/0369563 A1 | 12/2017 | Dubridge et al. |
| 2019/0070262 A1 | 3/2019 | Ring et al. |
| 2021/0015891 A1 | 1/2021 | Ring |
| 2022/0056091 A1 | 2/2022 | Pattabiraman et al. |
| 2023/0241172 A1 | 8/2023 | Ring et al. |
| 2023/0277625 A1 | 9/2023 | Ring et al. |
| 2023/0321192 A1 | 10/2023 | Ring et al. |
| 2023/0355714 A1 | 11/2023 | Ring et al. |
| 2023/0357342 A1 | 11/2023 | Pattabiraman et al. |

FOREIGN PATENT DOCUMENTS

| | | |
|---|---|---|
| CN | 102875675 A | 1/2013 |
| CN | 105051069 A | 11/2015 |
| EP | 1613274 B1 | 3/2010 |
| JP | 4024366 B2 | 12/2007 |
| JP | 4753867 B2 | 8/2011 |
| JP | 2014534978 T | 12/2014 |
| RU | 2593720 C2 | 8/2016 |
| WO | 199716203 A1 | 5/1997 |
| WO | 2004010957 A2 | 2/2004 |
| WO | 2005075648 A1 | 8/2005 |
| WO | 2005118642 A2 | 12/2005 |
| WO | 2006005910 A2 | 1/2006 |
| WO | 2013068571 A1 | 5/2013 |
| WO | 2014110601 A1 | 7/2014 |
| WO | 2018151868 A2 | 8/2018 |
| WO | 2022038417 A2 | 2/2022 |
| WO | 2022078524 A2 | 4/2022 |
| WO | 2022094473 A1 | 5/2022 |
| WO | 2022101826 A1 | 5/2022 |
| WO | 2023010021 A1 | 2/2023 |
| WO | 2023056193 A2 | 4/2023 |
| WO | 2023114829 A1 | 6/2023 |

(Continued)

OTHER PUBLICATIONS

Sonnet IL-18 Substitution Variants search, www.uniprot.org/uniprotkb/Q14116/entry.

Bessard et al., "High Antitumor Activity of RLI, and Interleukin-15 (IL-15)-IL-15 Receptor a Fusion Protein, in Metastatic Melanoma and Colorectal Cancer", Molecular Cancer Therapeutics v. 8, issue 9, p. 2736-45 (2009).

Boggio, K., et al., "Interleukin 12-Mediated Prevention of Spontaneous Mammary Adenocarcinomas in Two Lines of Her-2/neu Transgenic Mice", J. Exper. Med. v. 188, n. 3, p. 589-96 (1998).

Brunda, M.J., et al., "Antitumor and Antimetastatic Activity of Interleukin 12 Against Murine tumors" J. Exper Med v. 178, n. 4, p. 1223-30 (1993).

(Continued)

*Primary Examiner* — Prema M Mertz
(74) *Attorney, Agent, or Firm* — Morgan, Lewis & Bockius LLP

(57) ABSTRACT

Provided herein are variant human IL-18 (hIL-18) proteins and fusion proteins comprising the variant hIL-18 proteins. Such variant hIL-18 proteins exhibit biological IL-18 activity while having reduced or no detectable binding to inhibitory IL-18BP. Thus, in some embodiments, the variant hIL-18 proteins advantageously retain IL-18 biological activity in the presence of IL-18BP. Such variant hIL-18 and related fusion proteins find use, for example, in the treatment of cancer.

18 Claims, 11 Drawing Sheets
Specification includes a Sequence Listing.

(56) References Cited

FOREIGN PATENT DOCUMENTS

| WO | 2023118497 A1 | 6/2023 |
| WO | 2023161856 A1 | 8/2023 |

OTHER PUBLICATIONS

Cavallo et al., "Immune Events Associated with the Cure of Established Tumors and Spontaneous Metastases by Local and Systemic Interleukin 12", Cancer Res. v. 59, issue 2 p. 414-21 (1999).
Coughlin et al., "Interleukin-12 and Interleukin-18 Synergistically Induce Murine Tumor Regression which Involves Inhibition of Angiogenesis" J. Clinical Invest. v. 101, n. 6, p. 1441-1452 (1998).
Croce et al., "Sequential Immunogene Therapy with Interleukin-12- and Interleukin-15-Engineered Neuroblastoma Cells Cures Metastatic Disease in Syngeneic Mice", Clin Cancer Res., v. 11 (2), p. 735-742 (2005).
Cundall, M., "Production of Single-Chain Anti-Albumin Antibodies for Use in Protein Stabilization", Natl. Library of Canada, (Jan. 1, 1998), XP055476205, http://citeseerx.ist.psu.edu/viewdoc/download?doi=10.1.1628.9353&rep=rep1&typ=pdf.
Dave, E. et al., "Fab-dsFv: A bispecific antibody format with extended serum half-life through albumin binding", MABS, v. 8, n. 7, (Aug. 17, 2016).
Dietrich et al., "Complex Cancer Gene Therapy in Mice Melanoma" Langenbeck's Archives of Surgery, v. 387, issue 3-4, p. 177-182 (Jul. 2002).
Gao et al., "Mechanism of Action of IL-7 and its Potential Applications and Limitations in Cancer Immunotherapy", Int. J. Mol. Sci. v. 16, n. 5: 10267-10280 (2015).
Gu, Xin, et al., "Molecular Modeling and Affinity Determination of scFv Antibody: Proper linker Peptide Enhances its Activity", Annals of Biomedical Engineering, Kluwer academic Publishers-Plenum Publishers, NE, v. 38, n. 2, p. 537-549 (Oct. 9, 2009).
Kilinc et al., "Reversing Tumor Immune Suppression with Intratumoral IL-12: Activation of Tumor-Associated T Effector/Memory Cells, Induction of T Suppressor Apoptosis, and Infiltration of CD8+ T Effectors", J Immunol 177(10):6962-6973 (2006).
Lieschke et al., "Bioactive Murine and Human Interleukin-12 Fusion Proteins which Retain Antitumor Activity in vivo" Nature Biotechnology, v. 15, p. 35-40 (1997).
Mlecnik, B., et al., "Functional Network Pipeline Reveals Genetic Determinants Associated with in Situ Lymphocyte Proliferation and Survival of Cancer Patents", Sci Transl Med., v. 6, n. 228, p. 228ra37 (2014).
Muraoka, J. "Selection and Characterization of Human Serum Albumin-Specific Porcine scFv Antibodies Using a Phage Display Library", Monoclonal Antibodies in Immunodiagnosis and Immunotherapy, v. 33, n. 1, p. 42-48 (Feb. 1, 2014).
Nastala et al., "Recombinant IL-12 Administration Induces Tumor Regression in Association with IFN-Gamma Production", J Immunol., v. 153, n. 4, p. 1697-1706 (1994).
Rubinstein et al., "Converting IL-15 to a Superagonist by Binding to Soluble IL-15Ra", Proc Natl Acad Sci U.S.A., v.103, n. 24, p. 9166-71 (2006).
Subleski et al., "Enhanced Antitumor Response by Divergent Modulation of Natural Killer and Natural Killer T Cells in the Liver", Cancer Res v. 66, n. 22, p. 11005-11012 (2006).
Thyrell, L. et al., "Mechanisms of Interferon-Alpha Induced Apoptosis in Malignant Cells" Oncogene, v. 21, p. 1251-1262 (2002).
Weiner, G.J., "Building Better Monoclonal Antibody-Based Therapeutics", Nat Rev Cancer, v. 15(6): 361-370 (2015).
Wu, J., "IL-15 Agonists: The Cancer Cure Cytokine", J. Mol Genet Med, v. 7(4), 85 (2013).
Yu, W-G, et al., "Molecular Mechanisms Underlying IFN-γ-Mediated Tumor Growth Inhibition Induced during Tumor Immunotherapy with rIL-12", Inter. Immunol, v. 8, n. 6, p. 855-865 (1996).
Yusakul, Gorawit et al., "Effect of Linker Length Between Variable Domains of Single Chain Variable Fragment Antibody Against Daidzin on its Reactivity", Bioscience Biotechnology Biochemistry, v. 80, n. 7 p. 1306-1312 (Jul. 2, 2016).
Zhu, X. et al., "Novel Human Interleukin-15 Agonists", Journal of Immunology 183:3598-6007 (2009).
Zoller, M J, et al., Nucleic Acids Research, v. 10, n. 20, 1982, p. 6487-6500.
Ghandour H, et al., "Essential role for Rap1 GTPase and its guanine exchange factor CalDAG-GEFI in LFA-1 but not VLA-4 integrin mediated human T-cell adhesion", Blood,110(10):3682-90 (Nov. 15, 2007).
Colman P. M., "Effects of amino acid sequence changes on antibody-antigen interactions", Research in Immunology, v. 145, n. 1, p. 33-36, c.33 (1994).
Safdari Y. et al., "Antibody humanization methods—a review and update", Biotechnology and Genetic Engineering Reviews, v. 29, n. 2, p. 175-186, c.178,180 (2013).
Shen J. et al., "Single variable domain-IgG fusion: a novel recombinant approach to Fe domain-containing bispecific antibodies", Journal of Biological Chemistry, v. 281, n. 16, p. 10706-10714, c.10713 (2006).
Torres M. et al., "The immunoglobulin constant region contributes to affinity and specificity", Trends in immunology, v. 29, n. 2, p. 91-97, c.93-94 (2008).
Teplyakova et al., "Antibody modeling assessment II". Structures and models, Proteins: Structure, Function, and Bioinformatics, v. 82, n. 8, p. 1563-1582, Beeb TeKcT, c.1582 (2014).
Chen X. et al., "Fusion protein linkers: property, design and functionality", Advanced drug delivery reviews, v. 65, n. 10, p. 1357-1369, Beeb TeKCT, c.1365 (2013).
Maeda Y. et al., "Engineering of functional chimeric protein ••Vargula Luciferase, Analytical biochemistry", v. 249, n. 2, p. 147-152, Beeb TeKCT, c.148, c.151 (1997).
Office Action dated Feb. 26, 2024, issued in counterpart Australian Patent Application No. 2018220516 (8 pages).
Office Action dated Jul. 3, 2024, issued in counterpart Brazilian Patent Application No. 112019017001-4 (6 pages).
Office Action dated Apr. 3, 2024, issued in counterpart Canadian Patent Application No. 3,053,906 (5 pages).
Office Action and Search Report dated Aug. 3, 2023, issued in counterpart Chinese Patent Application No. 201880016019.1 (10 pages).
Office Action dated Mar. 11, 2022, issued in counterpart Japanese Patent Application No. 2019-566563 (13 pages).
Office Action dated Oct. 27, 2022, issued in counterpart New Zealand Patent Application No. 756674 (4 pages).
International Search Report dated Aug. 14, 2018, issued in counterpart International Patent Application No. PCT/US2018/000085 (8 pages).
Search Report dated Jul. 23, 2021, issued in counterpart Russian Federation Application No. 2019128690 (3 pages).
Office Action dated Jul. 29, 2021, issued in counterpart Russian Federation Patent Application No. 2019128690 (24 pages).
Office Action dated May 26, 2023, issued in counterpart New Zealand Patent Application No. 756674 (3 pages).
International Search Report dated Sep. 7, 2023, issued in counterpart International Patent Application No. PCT/US2023/067566 (5 pages).
International Search Report dated Jan. 19, 2024, issued in counterpart International Patent Application No. PCT/US2023/078366 (4 pages).
Office Action dated Jan. 12, 2021, issued in counterpart European Patent Application No. 18710585.3 (6 pages).

FIG. 1

Human IL-18 (Precursor protein)
MAAEPVEDNCINFVAMKFIDNTLYFIAEDDENLESDYFGKLESKLSVIRNLNDQVLFIDQGNRPLFEDMTDSD
CRDNAPRTIFIISMYKDSQPRGMAVTISVKCEKISTLSCENKIISFKEMNPPDNIKDTKSDIIFFQRSVPGHDNK
MQFESSSYEGYFLACEKERDLFKLILKKEDELGDRSIMFTVQNED (SEQ ID NO:1)

Human IL-18 (Mature Protein)
YFGKLESKLSVIRNLNDQVLFIDQGNRPLFEDMTDSDCRDNAPRTIFIISMYKDSQPRGMAVTISVKCEKISTLS
CENKIISFKEMNPPDNIKDTKSDIIFFQRSVPGHDNKMQFESSSYEGYFLACEKERDLFKLILKKEDELGDRSIM
FTVQNED (SEQ ID NO:2)

IL-18 Variant A
WFGKLESKLSVIRNLNDQVLFIDQGNRPLFEDMTDSDSRDNAPRTIFIISYYKDSQPRGWAVTISVKSEKISTLS
SENKIISFKEMNPPDNIKDTKSDIIFFQRSVPGHYNKMQFESSSYEGYFLASEKERDLFKLILKKEDELGDRSIMF
TVQNED (SEQ ID NO:3)

IL-18 Variant B
KFGKLESKLSVIRNLNDQVLFIDQGNRPLFEDMTDSDSRDNAPRTIFIISSYKDSQPRGWAVTISVKSEKISTLSS
ENKIISFKEMNPPDNIKDTKSDIIFFQREVPGHYNKMQFESSSYEGYFLASEKERDLFKLILKKEDELGDRSIMFT
VQNED (SEQ ID NO:4)

FIG. 2

A10m3 Albumin Binding Domain

| | Sequence | SEQ ID NO: |
|---|---|---|
| Variable heavy (vh) chain | EVQLVESGGGLIQPGRSLRLSCAASGITFDDAVMHWVRQAPGKGLEWVAGISSNSGYIGYADSVKGRFTISRDNAKNSLYLQMNRLRAEDTAVYYCVKGLYSNPRGGAFDIWGQGTMVTVSSAST | 5 |
| vhCDR1 | ITFDDAVMH | 6 |
| vhCDR2 | GISSNS | 7 |
| vhCDR3 | VKGLYSNPRGGAFDI | 8 |
| Variable light (vl) chain | VHSSYVLTQPPSVSVAPGQTATITCGGNNIGTKSVHWYQQKPGQAPVLVVYADSDRPSGIPERVSGSNSGNTATLTISRVEAGDEADYYCQVWDSRSDHLWVFGGGTKLTVLG | 9 |
| vlCDR1 | GGNNIGTKSVH | 10 |
| vlCDR2 | ADSDRPS | 11 |
| vlCDR3 | QVWDSRSDHLWV | 12 |
| A10m3 scFv | EVQLVESGGGLIQPGRSLRLSCAASGITFDDAVMHWVRQAPGKGLEWVAGISSNSGYIGYADSVKGRFTISRDNAKNSLYLQMNRLRAEDTAVYYCVKGLYSNPRGGAFDIWGQGTMVTVSSASTGGGGSGGGGSGGGGSVHSSYVLTQPPSVSVAPGQTATITCGGNNIGTKSVHWYQQKPGQAPVLVVYADSDRPSGIPERVSGSNSGNTATLTISRVEAGDEADYYCQVWDSRSDHLWVFGGGTKLTVLG | 13 |

FIG. 3

Human IL-12

IWELKKDVYVVELDWYPDAPGEMVVLTCDTPEEDGITWTLDQSSEVLGSGKTLTIQVKEFGDAGQYTCHKG
GEVLSHSLLLLHKKEDGIWSTDILKDQKEPKNKTFLRCEAKNYSGRFTCWWLTTISTDLTFSVKSSRGSSDPQG
VTCGAATLSAERVRGDNKEYEYSVECQEDSACPAAEESLPIEVMVDAVHKLKYENYTSSFFIRDIIKPDPPKNL
QLKPLKNSRQVEVSWEYPDTWSTPHSYFSLTFCVQVQGKSKREKKDRVFTDKTSATVICRKNASISVRAQDR
YYSSSWSEWASVPCS<u>GGGGGGS</u>RNLPVATPDPGMFPCLHHSQNLLRAVSNMLQKARQTLEFYPCTSEEIDH
EDITKDKTSTVEACLPLELTKNESCLNSRETSFITNGSCLASRKTSFMMALCLSSIYEDLKMYQVEFKTMNAKLL
MDPKRQIFLDQNMLAVIDELMQALNFNSETVPQKSSLEEPDFYKTKIKLCILLHAFRIRAVTIDRVTSYLNAS
(SEQ ID NO:14)

FIG. 4

| Name | Sequence | SEQ ID NO: |
|---|---|---|
| (GGGGS)$_1$ or GGGGS | GGGGS | 15 |
| (GGGGS)$_2$ | GGGGSGGGGS | 16 |
| (GGGGS)$_3$ | GGGGSGGGGSGGGGS | 17 |
| (GGGGS)$_4$ | GGGGSGGGGSGGGGSGGGGS | 18 |
| (GGGGS)$_5$ | GGGGSGGGGSGGGGSGGGGSGGGGS | 19 |
| (GGGGS)$_6$ | GGGGSGGGGSGGGGSGGGGS GGGGSGGGGS | 20 |
| (GGGGS)$_7$ | GGGGSGGGGSGGGGSGGGGSGGGGSGGGGSGGGGS | 21 |
| (GGGGA)$_1$ or GGGGA | GGGGA | 22 |
| (GGGGA)$_2$ | GGGGAGGGGA | 23 |
| (GGGGA)$_3$ | GGGGAGGGGAGGGGA | 24 |
| (GGGGA)$_4$ | GGGGAGGGGAGGGGAGGGGA | 25 |
| (GGGGA)$_5$ | GGGGAGGGGAGGGGAGGGGAGGGGA | 26 |
| (GGGGA)$_6$ | GGGGAGGGGAGGGGAGGGGAGGGGAGGGGA | 27 |
| (GGGGA)$_7$ | GGGGAGGGGAGGGGAGGGGAGGGGAGGGGAGGGGA | 28 |
| GGGGGGS | | 29 |

FIG. 5

Variant hIL-18 Albumin Binding Domain Fusion Protein (Variant A) (SEQ ID NO:30)

WFGKLESKLSVIRNLNDQVLFIDQGNRPLFEDMTDSDSRDNAPRTIFIISYYKDSQPRGWAVTISVKSEKISTLS
SENKIISFKEMNPPDNIKDTKSDIIFFQRSVPGHYNKMQFESSSYEGYFLASEKERDLFKLILKKEDELGDRSIMF
TVQNEDGGGGSGGGGSGGGGSGGGGSGGGGSEVQLVESGGGLIQPGRSLRLSCAASGITFDDAVMHWV
RQAPGKGLEWVAGISSNSGYIGYADSVKGRFTISRDNAKNSLYLQMNRLRAEDTAVYYCVKGLYSNPRGGAF
DIWGQGTMVTVSSASTGGGGSGGGGSGGGGSVHSSYVLTQPPSVSVAPGQTATITCGGNNIGTKSVHWY
QQKPGQAPVLVVYADSDRPSGIPERVSGSNSGNTATLTISRVEAGDEADYYCQVWDSRSDHLWVFGGGTKL
TVLG

Variant hIL-18 Albumin Binding Domain Fusion Protein (Variant A) (SEQ ID NO:31)

EVQLVESGGGLIQPGRSLRLSCAASGITFDDAVMHWVRQAPGKGLEWVAGISSNSGYIGYADSVKGRFTISR
DNAKNSLYLQMNRLRAEDTAVYYCVKGLYSNPRGGAFDIWGQGTMVTVSSASTGGGGSGGGGSGGGGS
VHSSYVLTQPPSVSVAPGQTATITCGGNNIGTKSVHWYQQKPGQAPVLVVYADSDRPSGIPERVSGSNSGN
TATLTISRVEAGDEADYYCQVWDSRSDHLWVFGGGTKLTVLGGGGGSGGGGSGGGGSGGGGSGGGGSW
FGKLESKLSVIRNLNDQVLFIDQGNRPLFEDMTDSDSRDNAPRTIFIISYYKDSQPRGWAVTISVKSEKISTLSSE
NKIISFKEMNPPDNIKDTKSDIIFFQRSVPGHYNKMQFESSSYEGYFLASEKERDLFKLILKKEDELGDRSIMFTV
QNED

Variant hIL-18 Albumin Binding Domain Fusion Protein (Variant B) (SEQ ID NO:32)

KFGKLESKLSVIRNLNDQVLFIDQGNRPLFEDMTDSDSRDNAPRTIFIISYKDSQPRGWAVTISVKSEKISTLSS
ENKIISFKEMNPPDNIKDTKSDIIFFQREVPGHYNKMQFESSSYEGYFLASEKERDLFKLILKKEDELGDRSIMFT
VQNEDGGGGSGGGGSGGGGSGGGGSGGGGSEVQLVESGGGLIQPGRSLRLSCAASGITFDDAVMHWVR
QAPGKGLEWVAGISSNSGYIGYADSVKGRFTISRDNAKNSLYLQMNRLRAEDTAVYYCVKGLYSNPRGGAFDI
WGQGTMVTVSSASTGGGGSGGGGSGGGGSVHSSYVLTQPPSVSVAPGQTATITCGGNNIGTKSVHWYQQ
KPGQAPVLVVYADSDRPSGIPERVSGSNSGNTATLTISRVEAGDEADYYCQVWDSRSDHLWVFGGGTKLTVL
G

Variant hIL-18 Albumin Binding Domain Fusion Protein (Variant B) (SEQ ID NO:33)

EVQLVESGGGLIQPGRSLRLSCAASGITFDDAVMHWVRQAPGKGLEWVAGISSNSGYIGYADSVKGRFTISR
DNAKNSLYLQMNRLRAEDTAVYYCVKGLYSNPRGGAFDIWGQGTMVTVSSASTGGGGSGGGGSGGGGS
VHSSYVLTQPPSVSVAPGQTATITCGGNNIGTKSVHWYQQKPGQAPVLVVYADSDRPSGIPERVSGSNSGN
TATLTISRVEAGDEADYYCQVWDSRSDHLWVFGGGTKLTVLGGGGGSGGGGSGGGGSGGGGSGGGGSKF
GKLESKLSVIRNLNDQVLFIDQGNRPLFEDMTDSDSRDNAPRTIFIISSYKDSQPRGWAVTISVKSEKISTLSSE
NKIISFKEMNPPDNIKDTKSDIIFFQREVPGHYNKMQFESSSYEGYFLASEKERDLFKLILKKEDELGDRSIMFTV
QNED

FIG. 6A hIL-12/Variant hIL-18 Albumin Binding Domain Fusion Protein (Variant A) (SEQ ID NO:34)

<u>MMSFVSLLLVGILFHATQA</u>IWELKKDVYVVELDWYPDAPGEMVVLTCDTPEEDGITWTLDQSSEVLGSGKTL
TIQVKEFGDAGQYTCHKGGEVLSHSLLLLHKKEDGIWSTDILKDQKEPKNKTFLRCEAKNYSGRFTCWWLTTI
STDLTFSVKSSRGSSDPQGVTCGAATLSAERVRGDNKEYEYSVECQEDSACPAAEESLPIEVMVDAVHKLKYE
NYTSSFFIRDIIKPDPPKNLQLKPLKNSRQVEVSWEYPDTWSTPHSYFSLTFCVQVQGKSKREKKDRVFTDKTS
ATVICRKNASISVRAQDRYYSSSWSEWASVPCSGGGGGGSRNLPVATPDPGMFPCLHHSQNLLRAVSNML
QKARQTLEFYPCTSEEIDHEDITKDKTSTVEACLPLELTKNESCLNSRETSFITNGSCLASRKTSFMMALCLSSIYE
DLKMYQVEFKTMNAKLLMDPKRQIFLDQNMLAVIDELMQALNFNSETVPQKSSLEEPDFYKTKIKLCILLHAF
RIRAVTIDRVTSYLNAS<u>GGGGSGGGGSGGGGSGGGGSGGGGS</u>EVQLVESGGGLIQPGRSLRLSCAASGITFD
DAVMHWVRQAPGKGLEWVAGISSNSGYIGYADSVKGRFTISRDNAKNSLYLQMNRLRAEDTAVYYCVKGL
YSNPRGGAFDIWGQGTMVTVSSASTGGGGSGGGGSGGGGSVHSSYVLTQPPSVSVAPGQTATITCGGNNI
GTKSVHWYQQKPGQAPVLVVYADSDRPSGIPERVSGSNSGNTATLTISRVEAGDEADYYCQVWDSRSDHL
WVFGGGTKLTVL<u>GGGGSGGGGSGGGGSGGGGSGGGGS</u>WFGKLESKLSVIRNLNDQVLFIDQGNRPLFE
DMTDSDSRDNAPRTIFIISYYKDSQPRGWAVTISVKSEKISTLSSENKIISFKEMNPPDNIKDTKSDIIFFQRSVP
GHYNKMQFESSSYEGYFLASEKERDLFKLILKKEDELGDRSIMFTVQNED hIL-12/Variant hIL-18 Albumin Binding Domain Fusion Protein (Variant B) (SEQ ID NO:35)

<u>MMSFVSLLLVGILFHATQA</u>IWELKKDVYVVELDWYPDAPGEMVVLTCDTPEEDGITWTLDQSSEVLGSGKTL
TIQVKEFGDAGQYTCHKGGEVLSHSLLLLHKKEDGIWSTDILKDQKEPKNKTFLRCEAKNYSGRFTCWWLTTI
STDLTFSVKSSRGSSDPQGVTCGAATLSAERVRGDNKEYEYSVECQEDSACPAAEESLPIEVMVDAVHKLKYE
NYTSSFFIRDIIKPDPPKNLQLKPLKNSRQVEVSWEYPDTWSTPHSYFSLTFCVQVQGKSKREKKDRVFTDKTS
ATVICRKNASISVRAQDRYYSSSWSEWASVPCSGGGGGGSRNLPVATPDPGMFPCLHHSQNLLRAVSNML
QKARQTLEFYPCTSEEIDHEDITKDKTSTVEACLPLELTKNESCLNSRETSFITNGSCLASRKTSFMMALCLSSIYE
DLKMYQVEFKTMNAKLLMDPKRQIFLDQNMLAVIDELMQALNFNSETVPQKSSLEEPDFYKTKIKLCILLHAF
RIRAVTIDRVTSYLNAS<u>GGGGSGGGGSGGGGSGGGGSGGGGS</u>EVQLVESGGGLIQPGRSLRLSCAASGITFD
DAVMHWVRQAPGKGLEWVAGISSNSGYIGYADSVKGRFTISRDNAKNSLYLQMNRLRAEDTAVYYCVKGL
YSNPRGGAFDIWGQGTMVTVSSASTGGGGSGGGGSGGGGSVHSSYVLTQPPSVSVAPGQTATITCGGNNI
GTKSVHWYQQKPGQAPVLVVYADSDRPSGIPERVSGSNSGNTATLTISRVEAGDEADYYCQVWDSRSDHL
WVFGGGTKLTVL<u>GGGGSGGGGSGGGGSGGGGSGGGGS</u>KFGKLESKLSVIRNLNDQVLFIDQGNRPLFED
MTDSD<u>S</u>RDNAPRTIFIIS<u>S</u>YKDSQPRG<u>W</u>AVTISVK<u>S</u>EKISTLS<u>S</u>ENKIISFKEMNPPDNIKDTKSDIIFFQR<u>E</u>VPG
H<u>Y</u>NKMQFESSSYEGYFLA<u>S</u>EKERDLFKLILKKEDELGDRSIMFTVQNED

FIG. 6B

Variant hIL-18/hIL-12 Albumin Binding Domain Fusion Protein (Variant A) (SEQ ID NO:36)

MMSFVSLLLVGILFHATQAWFGKLESKLSVIRNLNDQVLFIDQGNRPLFEDMTDSDSRDNAPRTIFIISYYKDS
QPRGWAVTISVKSEKISTLSSENKIISFKEMNPPDNIKDTKSDIIFFQRSVPGHYNKMQFESSSYEGYFLASEKE
RDLFKLILKKEDELGDRSIMFTVQNEDGGGGSGGGGSGGGGSGGGGSGGGGSEVQLVESGGGLIQPGRSLR
LSCAASGITFDDAVMHWVRQAPGKGLEWVAGISSNSGYIGYADSVKGRFTISRDNAKNSLYLQMNRLRAED
TAVYYCVKGLYSNPRGGAFDIWGQGTMVTVSSASTGGGGSGGGGSGGGGSVHSSYVLTQPPSVSVAPGQT
ATITCGGNNIGTKSVHWYQQKPGQAPVLVVYADSDRPSGIPERVSGSNSGNTATLTISRVEAGDEADYYCQV
WDSRSDHLWVFGGGTKLTVLGGGGSGGGGSGGGGSGGGGSGGGGSIWELKKDVYVVELDWYPDAPG
EMVVLTCDTPEEDGITWTLDQSSEVLGSGKTLTIQVKEFGDAGQYTCHKGGEVLSHSLLLLHKKEDGIWSTDI
LKDQKEPKNKTFLRCEAKNYSGRFTCWWLTTISTDLTFSVKSSRGSSDPQGVTCGAATLSAERVRGDNKEYEY
SVECQEDSACPAAEESLPIEVMVDAVHKLKYENYTSSFFIRDIIKPDPPKNLQLKPLKNSRQVEVSWEYPDTWS
TPHSYFSLTFCVQVQGKSKREKKDRVFTDKTSATVICRKNASISVRAQDRYYSSSWSEWASVPCSGGGGGGS
RNLPVATPDPGMFPCLHHSQNLLRAVSNMLQKARQTLEFYPCTSEEIDHEDITKDKTSTVEACLPLELTKNES
CLNSRETSFITNGSCLASRKTSFMMALCLSSIYEDLKMYQVEFKTMNAKLLMDPKRQIFLDQNMLAVIDELM
QALNFNSETVPQKSSLEEPDFYKTKIKLCILLHAFRIRAVTIDRVTSYLNAS

Variant hIL-18/hIL-12 Albumin Binding Domain Fusion Protein (Variant B) (SEQ ID NO:37)

MMSFVSLLLVGILFHATQAKFGKLESKLSVIRNLNDQVLFIDQGNRPLFEDMTDSDSRDNAPRTIFIISSYKDSQ
PRGWAVTISVKSEKISTLSSENKIISFKEMNPPDNIKDTKSDIIFFQREVPGHYNKMQFESSSYEGYFLASEKERD
LFKLILKKEDELGDRSIMFTVQNEDGGGGSGGGGSGGGGSGGGGSGGGGSEVQLVESGGGLIQPGRSLRLS
CAASGITFDDAVMHWVRQAPGKGLEWVAGISSNSGYIGYADSVKGRFTISRDNAKNSLYLQMNRLRAEDTA
VYYCVKGLYSNPRGGAFDIWGQGTMVTVSSASTGGGGSGGGGSGGGGSVHSSYVLTQPPSVSVAPGQTATI
TCGGNNIGTKSVHWYQQKPGQAPVLVVYADSDRPSGIPERVSGSNSGNTATLTISRVEAGDEADYYCQVWDS
RSDHLWVFGGGTKLTVLGGGGSGGGGSGGGGSGGGGSGGGGSIWELKKDVYVVELDWYPDAPGEMVV
LTCDTPEEDGITWTLDQSSEVLGSGKTLTIQVKEFGDAGQYTCHKGGEVLSHSLLLLHKKEDGIWSTDILKDQK
EPKNKTFLRCEAKNYSGRFTCWWLTTISTDLTFSVKSSRGSSDPQGVTCGAATLSAERVRGDNKEYEYSVECQ
EDSACPAAEESLPIEVMVDAVHKLKYENYTSSFFIRDIIKPDPPKNLQLKPLKNSRQVEVSWEYPDTWSTPHSY
FSLTFCVQVQGKSKREKKDRVFTDKTSATVICRKNASISVRAQDRYYSSSWSEWASVPCSGGGGGGSRNLPV
ATPDPGMFPCLHHSQNLLRAVSNMLQKARQTLEFYPCTSEEIDHEDITKDKTSTVEACLPLELTKNESCLNSRE
TSFITNGSCLASRKTSFMMALCLSSIYEDLKMYQVEFKTMNAKLLMDPKRQIFLDQNMLAVIDELMQALNFN
SETVPQKSSLEEPDFYKTKIKLCILLHAFRIRAVTIDRVTSYLNAS

FIG. 7
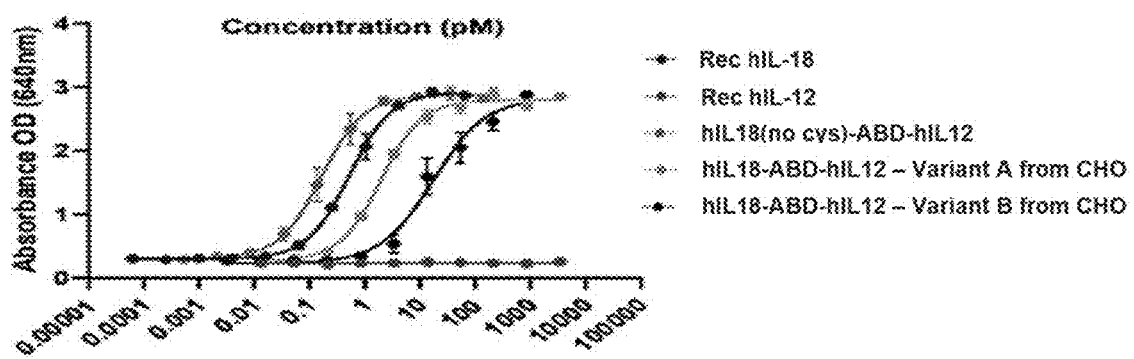
FIG. 8A-C
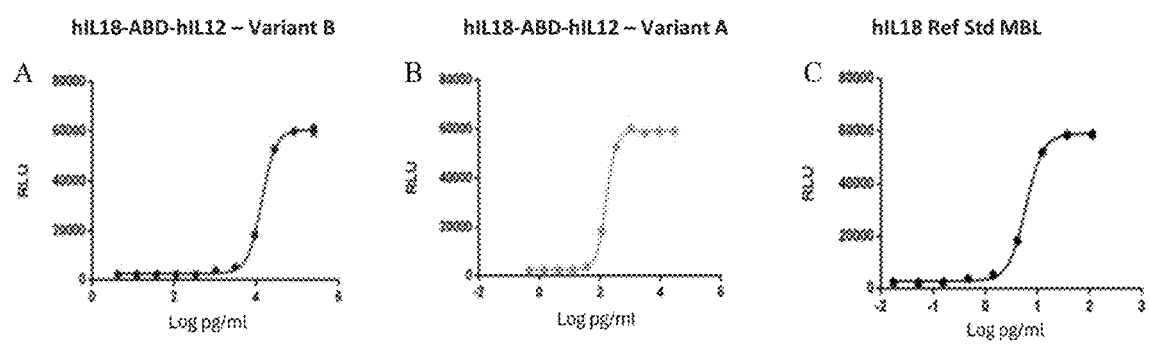

FIG. 9C
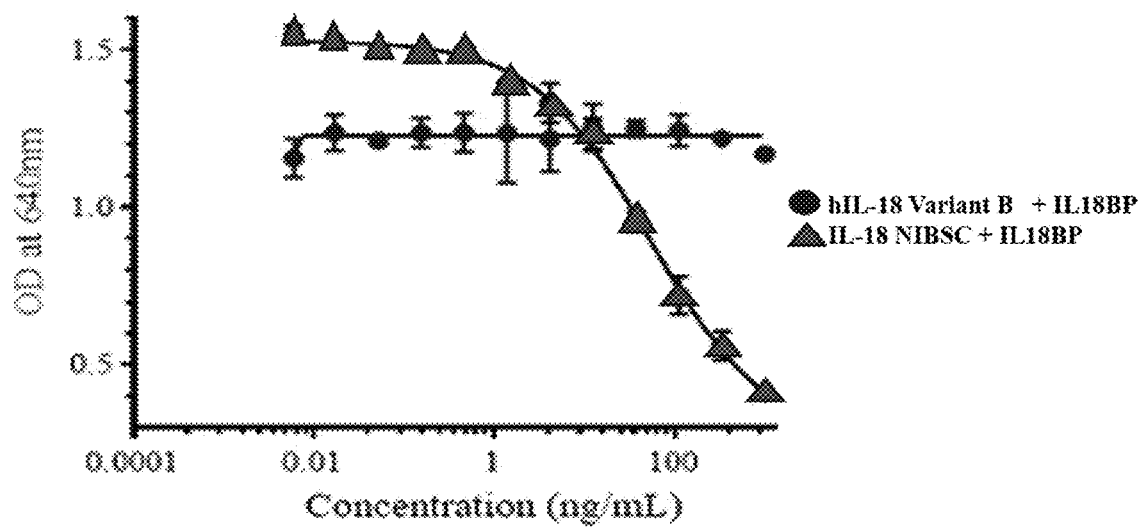
FIG. 10A-B
Surface Plasmon Resonance (SPR) measurement of hIL18BP binding
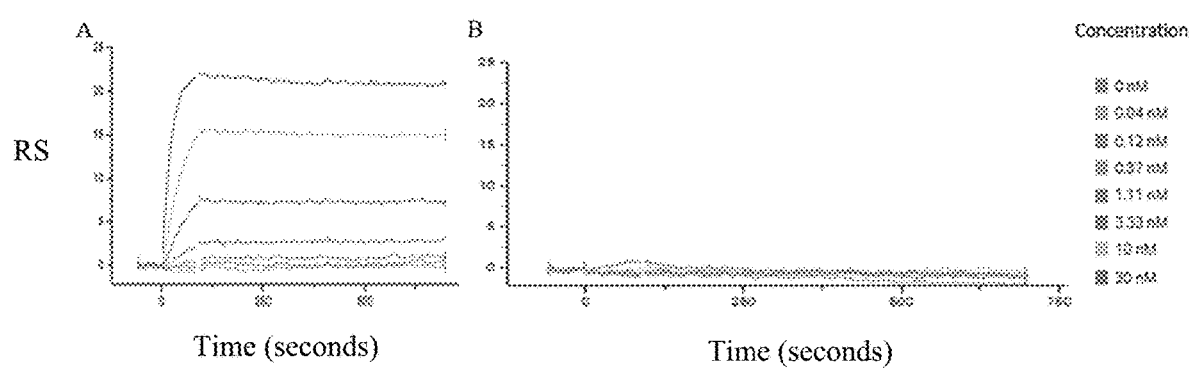

IL18 Variant A Bioactivity HEK-Blue™IL-12 Receptor Reporter Assay

```
                             SEQUENCE LISTING

Sequence total quantity: 37
SEQ ID NO: 1            moltype = AA  length = 193
FEATURE                 Location/Qualifiers
source                  1..193
                        mol_type = protein
                        organism = Homo sapiens
SEQUENCE: 1
MAAEPVEDNC INFVAMKFID NTLYFIAEDD ENLESDYFGK LESKLSVIRN LNDQVLFIDQ   60
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NED                                                     193

SEQ ID NO: 2            moltype = AA  length = 157
FEATURE                 Location/Qualifiers
source                  1..157
                        mol_type = protein
                        organism = Homo sapiens
SEQUENCE: 2
YFGKLESKLS VIRNLNDQVL FIDQGNRPLF EDMTDSDCRD NAPRTIFIIS MYKDSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 3            moltype = AA  length = 157
FEATURE                 Location/Qualifiers
source                  1..157
                        mol_type = protein
                        organism = synthetic construct
SEQUENCE: 3
WFGKLESKLS VIRNLNDQVL FIDQGNRPLF EDMTDSDSRD NAPRTIFIIS YYKDSQPRGW   60
AVTISVKSEK ISTLSSENKI ISFKEMNPPD NIKDTKSDII FFQRSVPGHY NKMQFESSSY  120
EGYFLASEKE RDLFKLILKK EDELGDRSIM FTVQNED                           157

SEQ ID NO: 4            moltype = AA  length = 157
FEATURE                 Location/Qualifiers
source                  1..157
                        mol_type = protein
                        organism = synthetic construct
SEQUENCE: 4
KFGKLESKLS VIRNLNDQVL FIDQGNRPLF EDMTDSDSRD NAPRTIFIIS SYKDSQPRGW   60
AVTISVKSEK ISTLSSENKI ISFKEMNPPD NIKDTKSDII FFQREVPGHY NKMQFESSSY  120
EGYFLASEKE RDLFKLILKK EDELGDRSIM FTVQNED                           157

SEQ ID NO: 5            moltype = AA  length = 125
FEATURE                 Location/Qualifiers
source                  1..125
                        mol_type = protein
                        organism = synthetic construct
SEQUENCE: 5
EVQLVESGGG LIQPGRSLRL SCAASGITFD DAVMHWVRQA PGKGLEWVAG ISSNSGYIGY   60
ADSVKGRFTI SRDNAKNSLY LQMNRLRAED TAVYYCVKGL YSNPRGGAFD IWGQGTMVTV  120
SSAST                                                              125
```

```
SEQ ID NO: 6              moltype = AA    length = 9
FEATURE                   Location/Qualifiers
source                    1..9
                          mol_type = protein
                          organism = synthetic construct
SEQUENCE: 6
ITFDDAVMH                                                                    9

SEQ ID NO: 7              moltype = AA    length = 6
FEATURE                   Location/Qualifiers
source                    1..6
                          mol_type = protein
                          organism = synthetic construct
SEQUENCE: 7
GISSNS                                                                       6

SEQ ID NO: 8              moltype = AA    length = 15
FEATURE                   Location/Qualifiers
source                    1..15
                          mol_type = protein
                          organism = synthetic construct
SEQUENCE: 8
VKGLYSNPRG GAFDI                                                            15

SEQ ID NO: 9              moltype = AA    length = 113
FEATURE                   Location/Qualifiers
source                    1..113
                          mol_type = protein
                          organism = synthetic construct
SEQUENCE: 9
VHSSYVLTQP PSVSVAPGQT ATITCGGNNI GTKSVHWYQQ KPGQAPVLVV YADSDRPSGI            60
PERVSGSNSG NTATLTISRV EAGDEADYYC QVWDSRSDHL WVFGGGTKLT VLG                  113

SEQ ID NO: 10             moltype = AA    length = 11
FEATURE                   Location/Qualifiers
source                    1..11
                          mol_type = protein
                          organism = synthetic construct
SEQUENCE: 10
GGNNIGTKSV H                                                                11

SEQ ID NO: 11             moltype = AA    length = 7
FEATURE                   Location/Qualifiers
source                    1..7
                          mol_type = protein
                          organism = synthetic construct
SEQUENCE: 11
ADSDRPS                                                                      7

SEQ ID NO: 12             moltype = AA    length = 12
FEATURE                   Location/Qualifiers
source                    1..12
                          mol_type = protein
                          organism = synthetic construct
SEQUENCE: 12
QVWDSRSDHL WV                                                               12

SEQ ID NO: 13             moltype = AA    length = 253
FEATURE                   Location/Qualifiers
source                    1..253
                          mol_type = protein
                          organism = synthetic construct
SEQUENCE: 13
EVQLVESGGG LIQPGRSLRL SCAASGITFD DAVMHWVRQA PGKGLEWVAG ISSNSGYIGY            60
ADSVKGRFTI SRDNAKNSLY LQMNRLRAED TAVYYCVKGL YSNPRGGAFD IWGQGTMVTV           120
SSASTGGGGS GGGGSGGGGS VHSSYVLTQP PSVSVAPGQT ATITCGGNNI GTKSVHWYQQ           180
KPGQAPVLVV YADSDRPSGI PERVSGSNSG NTATLTISRV EAGDEADYYC QVWDSRSDHL           240
WVFGGGTKLT VLG                                                              253

SEQ ID NO: 14             moltype = AA    length = 510
FEATURE                   Location/Qualifiers
source                    1..510
                          mol_type = protein
                          organism = Homo sapiens
SEQUENCE: 14
IWELKKDVYV VELDWYPDAP GEMVVLTCDT PEEDGITWTL DQSSEVLGSG KTLTIQVKEF            60
GDAGQYTCHK GGEVLSHSLL LLHKKEDGIW STDILKDQKE PKNKTFLRCE AKNYSGRFTC           120
WWLTTISTDL TFSVKSSRGS SDPQGVTCGA ATLSAERVRG DNKEYEYSVE CQEDSACPAA           180
EESLPIEVMV DAVHKLKYEN YTSSFFIRDI IKPDPPKNLQ LKPLKNSRQV EVSWEYPDTW           240
```

```
STPHSYFSLT FCVQVQGKSK REKKDRVFTD KTSATVICRK NASISVRAQD RYYSSSWSEW  300
ASVPCSGGGG GGSRNLPVAT PDPGMFPCLH HSQNLLRAVS NMLQKARQTL EFYPCTSEEI  360
DHEDITKDKT STVEACLPLE LTKNESCLNS RETSFITNGS CLASRKTSFM MALCLSSIYE  420
DLKMYQVEFK TMNAKLLMDP KRQIFLDQNM LAVIDELMQA LNFNSETVPQ KSSLEEPDFY  480
KTKIKLCILL HAFRIRAVTI DRVTSYLNAS                                  510

SEQ ID NO: 15            moltype = AA   length = 5
FEATURE                  Location/Qualifiers
source                   1..5
                         mol_type = protein
                         organism = synthetic construct
SEQUENCE: 15
GGGGS                                                             5

SEQ ID NO: 16            moltype = AA   length = 10
FEATURE                  Location/Qualifiers
source                   1..10
                         mol_type = protein
                         organism = synthetic construct
SEQUENCE: 16
GGGGSGGGGS                                                        10

SEQ ID NO: 17            moltype = AA   length = 15
FEATURE                  Location/Qualifiers
source                   1..15
                         mol_type = protein
                         organism = synthetic construct
SEQUENCE: 17
GGGGSGGGGS GGGGS                                                  15

SEQ ID NO: 18            moltype = AA   length = 20
FEATURE                  Location/Qualifiers
source                   1..20
                         mol_type = protein
                         organism = synthetic construct
SEQUENCE: 18
GGGGSGGGGS GGGGSGGGGS                                             20

SEQ ID NO: 19            moltype = AA   length = 25
FEATURE                  Location/Qualifiers
source                   1..25
                         mol_type = protein
                         organism = synthetic construct
SEQUENCE: 19
GGGGSGGGGS GGGGSGGGGS GGGGS                                       25

SEQ ID NO: 20            moltype = AA   length = 30
FEATURE                  Location/Qualifiers
source                   1..30
                         mol_type = protein
                         organism = synthetic construct
SEQUENCE: 20
GGGGSGGGGS GGGGSGGGGS GGGGSGGGGS                                  30

SEQ ID NO: 21            moltype = AA   length = 35
FEATURE                  Location/Qualifiers
source                   1..35
                         mol_type = protein
                         organism = synthetic construct
SEQUENCE: 21
GGGGSGGGGS GGGGSGGGGS GGGGSGGGGS GGGGS                            35

SEQ ID NO: 22            moltype = AA   length = 5
FEATURE                  Location/Qualifiers
source                   1..5
                         mol_type = protein
                         organism = synthetic construct
SEQUENCE: 22
GGGGA                                                             5

SEQ ID NO: 23            moltype = AA   length = 10
FEATURE                  Location/Qualifiers
source                   1..10
                         mol_type = protein
                         organism = synthetic construct
SEQUENCE: 23
GGGGAGGGGA                                                        10

SEQ ID NO: 24            moltype = AA   length = 15
```

```
FEATURE                 Location/Qualifiers
source                  1..15
                        mol_type = protein
                        organism = synthetic construct
SEQUENCE: 24
GGGGAGGGGA GGGGA                                                           15

SEQ ID NO: 25           moltype = AA   length = 20
FEATURE                 Location/Qualifiers
source                  1..20
                        mol_type = protein
                        organism = synthetic construct
SEQUENCE: 25
GGGGAGGGGA GGGGAGGGGA                                                      20

SEQ ID NO: 26           moltype = AA   length = 25
FEATURE                 Location/Qualifiers
source                  1..25
                        mol_type = protein
                        organism = synthetic construct
SEQUENCE: 26
GGGGAGGGGA GGGGAGGGGA GGGGA                                                25

SEQ ID NO: 27           moltype = AA   length = 30
FEATURE                 Location/Qualifiers
source                  1..30
                        mol_type = protein
                        organism = synthetic construct
SEQUENCE: 27
GGGGAGGGGA GGGGAGGGGA GGGGAGGGGA                                           30

SEQ ID NO: 28           moltype = AA   length = 35
FEATURE                 Location/Qualifiers
source                  1..35
                        mol_type = protein
                        organism = synthetic construct
SEQUENCE: 28
GGGGAGGGGA GGGGAGGGGA GGGGAGGGGA GGGGA                                     35

SEQ ID NO: 29           moltype = AA   length = 7
FEATURE                 Location/Qualifiers
source                  1..7
                        mol_type = protein
                        organism = synthetic construct
SEQUENCE: 29
GGGGGGS                                                                     7

SEQ ID NO: 30           moltype = AA   length = 435
FEATURE                 Location/Qualifiers
source                  1..435
                        mol_type = protein
                        organism = synthetic construct
SEQUENCE: 30
WFGKLESKLS VIRNLNDQVL FIDQGNRPLF EDMTDSDSRD NAPRTIFIIS YYKDSQPRGW           60
AVTISVKSEK ISTLSSENKI ISFKEMNPPD NIKDTKSDII FFQRSVPGHY NKMQFESSSY          120
EGYFLASEKE RDLFKLILKK EDELGDRSIM FTVQNEDGGG GSGGGGSGGG GSGGGGSGGG          180
GSEVQLVESG GGLIQPGRSL RLSCAASGIT FDDAVMHWVR QAPGKGLEWV AGISSNSGYI          240
GYADSVKGRF TISRDNAKNS LYLQMNRLRA EDTAVYYCVK GLYSNPRGGA FDIWGQGTMV          300
TVSSASTGGG GSGGGGSGGG GSVHSSYVLT QPPSVSVAPG QTATITCGGN NIGTKSVHWY          360
QQKPGQAPVL VVYADSDRPS GIPERVSGSN SGNTATLTIS RVEAGDEADY YCQVWDSRSD          420
HLWVFGGGTK LTVLG                                                          435

SEQ ID NO: 31           moltype = AA   length = 435
FEATURE                 Location/Qualifiers
source                  1..435
                        mol_type = protein
                        organism = synthetic construct
SEQUENCE: 31
EVQLVESGGG LIQPGRSLRL SCAASGITFD DAVMHWVRQA PGKGLEWVAG ISSNSGYIGY           60
ADSVKGRFTI SRDNAKNSLY LQMNRLRAED TAVYYCVKGL YSNPRGGAFD IWGQGTMVTV          120
SSASTGGGGS GGGGSGGGGS VHSSYVLTQP PSVSVAPGQT ATITCGGNNI GTKSVHWYQQ          180
KPGQAPVLVV YADSDRPSGI PERVSGSNSG NTATLTISRV EAGDEADYYC QVWDSRSDHL          240
WVFGGGTKLT VLGGGGGSGG GSGGGGSGG GGSGGGGSWF GKLESKLSVI RNLNDQVLFI           300
DQGNRPLFED MTDSDSRDNA PRTIFIISYY KDSQPRGWAV TISVKSEKIS TLSSENKIIS          360
FKEMNPPDNI KDTKSDIIFF QRSVPGHYNK MQFESSSYEG YFLASEKERD LFKLILKKED          420
ELGDRSIMFT VQNED                                                          435

SEQ ID NO: 32           moltype = AA   length = 435
FEATURE                 Location/Qualifiers
```

```
source                          1..435
                                mol_type = protein
                                organism = synthetic construct
SEQUENCE: 32
KFGKLESKLS VIRNLNDQVL FIDQGNRPLF EDMTDSDSRD NAPRTIFIIS SYKDSQPRGW    60
AVTISVKSEK ISTLSSENKI ISFKEMNPPD NIKDTKSDII FFQREVPGHY NKMQFESSSY   120
EGYFLASEKE RDLFKLILKK EDELGDRSIM FTVQNEDGGG GSGGGGSGGG GSGGGGSGGG   180
GSEVQLVESG GGLIQPGRSL RLSCAASGIT FDDAVMHWVR QAPGKGLEWV AGISSNSGYI   240
GYADSVKGRF TISRDNAKNS LYLQMNRLRA EDTAVYYCVK GLYSNPRGGA FDIWGQGTMV   300
TVSSASTGGG GSGGGGSGGG GSVHSSYVLT QPPSVSVAPG QTATITCGGN NIGTKSVHWY   360
QQKPGQAPVL VVYADSDRPS GIPERVSGSN SGNTATLTIS RVEAGDEADY YCQVWDSRSD   420
HLWVFGGGTK LTVLG                                                    435

SEQ ID NO: 33                   moltype = AA  length = 435
FEATURE                         Location/Qualifiers
source                          1..435
                                mol_type = protein
                                organism = synthetic construct
SEQUENCE: 33
EVQLVESGGG LIQPGRSLRL SCAASGITFD DAVMHWVRQA PGKGLEWVAG ISSNSGYIGY    60
ADSVKGRFTI SRDNAKNSLY LQMNRLRAED TAVYYCVKGL YSNPRGGAFD IWGQGTMVTV   120
SSASTGGGGS GGGGSGGGGS VHSSYVLTQP PSVSVAPGQT ATITCGGNNI GTKSVHWYQQ   180
KPGQAPVLVV YADSDRPSGI PERVSGSNSG NTATLTISRV EAGDEADYYC QVWDSRSDHL   240
WVFGGGTKLT VLGGGGSGG GGSGGGGSGG GGSGGGGSKF GKLESKLSVI RNLNDQVLFI   300
DQGNRPLFED MTDSDSRDNA PRTIFIISSY KDSQPRGWAV TISVKSEKIS TLSSENKIIS   360
FKEMNPPDNI KDTKSDIIFF QREVPGHYNK MQFESSSYEG YFLASEKERD LFKLILKKED   420
ELGDRSIMFT VQNED                                                    435

SEQ ID NO: 34                   moltype = AA  length = 989
FEATURE                         Location/Qualifiers
source                          1..989
                                mol_type = protein
                                organism = synthetic construct
SEQUENCE: 34
MMSFVSLLLV GILFHATQAI WELKKDVYVV ELDWYPDAPG EMVVLTCDTP EEDGITWTLD    60
QSSEVLGSGK TLTIQVKEFG DAGQYTCHKG GEVLSHSLLL LHKKEDGIWS TDILKDQKEP   120
KNKTFLRCEA KNYSGRFTCW WLTTISTDLT FSVKSSRGSS DPQGVTCGAA TLSAERVRGD   180
NKEYEYSVEC QEDSACPAAE ESLPIEVMVD AVHKLKYENY TSSFFIRDII KPDPPKNLQL   240
KPLKNSRQVE VSWEYPDTWS TPHSYFSLTF CVQVQGKSKR EKKDRVFTDK TSATVICRKN   300
ASISVRAQDR YYSSSWSEWA SVPCSGGGGG GSRNLPVATP DPGMFPCLHH SQNLLRAVSN   360
MLQKARQTLE FYPCTSEEID HEDITKDKTS TVEACLPLEL TKNESCLNSR ETSFITNGSC   420
LASRKTSFMM ALCLSSIYED LKMYQVEFKT MNAKLLMDPK RQIFLDQNML AVIDELMQAL   480
NFNSETVPQK SSLEEPDFYK TKIKLCILLH AFRIRAVTID RVTSYLNASG GGGSGGGGSG   540
GGGSEVQLVE SGGGLIQPGR SLRLSCAASG ITFDDAVMHW VRQAPGKGLE             600
WVAGISSNSG YIGYADSVKG RFTISRDNAK NSLYLQMNRL RAEDTAVYYC VKGLYSNPRG   660
GAFDIWGQGT MVTVSSASTG GGGSGGGGSG GGSVHSSYV LTQPPSVSVA PGQTATITCG   720
GNNIGTKSVH WYQQKPGQAP VLVVYADSDR PSGIPERVSG SNSGNTATLT ISRVEAGDEA   780
DYYCQVWDSR SDHLWVFGGG TKLTVLGGGG SGGGGSGGGG GSGGGGSGGG GSWFGKLESK   840
LSVIRNLNDQ VLFIDQGNRP LFEDMTDSDS RDNAPRTIFI ISYYKDSQPR GWAVTISVKS   900
EKISTLSSEN KIISFKEMNP PDNIKDTKSD IIFFQRSVPG HYNKMQFESS SYEGYFLASE   960
KERDLFKLIL KKEDELGDRS IMFTVQNED                                     989

SEQ ID NO: 35                   moltype = AA  length = 989
FEATURE                         Location/Qualifiers
source                          1..989
                                mol_type = protein
                                organism = synthetic construct
SEQUENCE: 35
MMSFVSLLLV GILFHATQAI WELKKDVYVV ELDWYPDAPG EMVVLTCDTP EEDGITWTLD    60
QSSEVLGSGK TLTIQVKEFG DAGQYTCHKG GEVLSHSLLL LHKKEDGIWS TDILKDQKEP   120
KNKTFLRCEA KNYSGRFTCW WLTTISTDLT FSVKSSRGSS DPQGVTCGAA TLSAERVRGD   180
NKEYEYSVEC QEDSACPAAE ESLPIEVMVD AVHKLKYENY TSSFFIRDII KPDPPKNLQL   240
KPLKNSRQVE VSWEYPDTWS TPHSYFSLTF CVQVQGKSKR EKKDRVFTDK TSATVICRKN   300
ASISVRAQDR YYSSSWSEWA SVPCSGGGGG GSRNLPVATP DPGMFPCLHH SQNLLRAVSN   360
MLQKARQTLE FYPCTSEEID HEDITKDKTS TVEACLPLEL TKNESCLNSR ETSFITNGSC   420
LASRKTSFMM ALCLSSIYED LKMYQVEFKT MNAKLLMDPK RQIFLDQNML AVIDELMQAL   480
NFNSETVPQK SSLEEPDFYK TKIKLCILLH AFRIRAVTID RVTSYLNASG GGGSGGGGSG   540
GGGSGGGGSG GGGSEVQLVE SGGGLIQPGR SLRLSCAASG ITFDDAVMHW VRQAPGKGLE   600
WVAGISSNSG YIGYADSVKG RFTISRDNAK NSLYLQMNRL RAEDTAVYYC VKGLYSNPRG   660
GAFDIWGQGT MVTVSSASTG GGGSGGGGSG GGSVHSSYV LTQPPSVSVA PGQTATITCG   720
GNNIGTKSVH WYQQKPGQAP VLVVYADSDR PSGIPERVSG SNSGNTATLT ISRVEAGDEA   780
DYYCQVWDSR SDHLWVFGGG TKLTVLGGGG SGGGGSGGG GSGGGGSGGG GSKFGKLESK   840
LSVIRNLNDQ VLFIDQGNRP LFEDMTDSDS RDNAPRTIFI ISYKDSQPR GWAVTISVKS    900
EKISTLSSEN KIISFKEMNP PDNIKDTKSD IIFFQREVPG HYNKMQFESS SYEGYFLASE   960
KERDLFKLIL KKEDELGDRS IMFTVQNED                                     989

SEQ ID NO: 36                   moltype = AA  length = 989
FEATURE                         Location/Qualifiers
source                          1..989
```

-continued

```
                       mol_type = protein
                       organism = synthetic construct
SEQUENCE: 36
MMSFVSLLLV GILFHATQAW FGKLESKLSV IRNLNDQVLF IDQGNRPLFE DMTDSDSRDN  60
APRTIFIISY YKDSQPRGWA VTISVKSEKI STLSSENKII SFKEMNPPDN IKDTKSDIIF  120
FQRSVPGHYN KMQFESSSYE GYFLASEKER DLFKLILKKE DELGDRSIMF TVQNEDGGGG  180
SGGGGSGGGG SGGGGSGGGG SEVQLVESGG GLIQPGRSLR LSCAASGITF DDAVMHWVRQ  240
APGKGLEWVA GISSNSGYIG YADSVKGRFT ISRDNAKNSL YLQMNRLRAE DTAVYYCVKG  300
LYSNPRGGAF DIWGQGTMVT VSSASTGGGG SGGGGSGGGG SVHSSYVLTQ PPSVSVAPGQ  360
TATITCGGNN IGTKSVHWYQ QKPGQAPVLV VYADSDRPSG IPERVSGSNS GNTATLTISR  420
VEAGDEADYY CQVWDSRSDH LWVFGGGTKL TVLGGGGGSG GGGSGGGGSG GGGSGGGGSI  480
WELKKDVYVV ELDWYPDAPG EMVVLTCDTP EEDGITWTLD QSSEVLGSGK TLTIQVKEFG  540
DAGQYTCHKG GEVLSHSLLL LHKKEDGIWS TDILKDQKEP KNKTFLRCEA KNYSGRFTCW  600
WLTTISTDLT FSVKSSRGSS DPQGVTCGAA TLSAERVRGD NKEYEYSVEC QEDSACPAAE  660
ESLPIEVMVD AVHKLKYENY TSSFFIRDII KPDPPKNLQL KPLKNSRQVE VSWEYPDTWS  720
TPHSYFSLTF CVQVQGKSKR EKKDRVFTDK TSATVICRKN ASISVRAQDR YYSSSWSEWA  780
SVPCSGGGGG GSRNLPVATP DPGMFPCLHH SQNLLRAVSN MLQKARQTLE FYPCTSEEID  840
HEDITKDKTS TVEACLPLEL TKNESCLNSR ETSFITNGSC LASRKTSFMM ALCLSSIYED  900
LKMYQVEFKT MNAKLLMDPK RQIFLDQNML AVIDELMQAL NFNSETVPQK SSLEEPDFYK  960
TKIKLCILLH AFRIRAVTID RVTSYLNAS                                    989

SEQ ID NO: 37          moltype = AA  length = 989
FEATURE                Location/Qualifiers
source                 1..989
                       mol_type = protein
                       organism = synthetic construct
SEQUENCE: 37
MMSFVSLLLV GILFHATQAK FGKLESKLSV IRNLNDQVLF IDQGNRPLFE DMTDSDSRDN  60
APRTIFIISS YKDSQPRGWA VTISVKSEKI STLSSENKII SFKEMNPPDN IKDTKSDIIF  120
FQREVPGHYN KMQFESSSYE GYFLASEKER DLFKLILKKE DELGDRSIMF TVQNEDGGGG  180
SGGGGSGGGG SGGGGSGGGG SEVQLVESGG GLIQPGRSLR LSCAASGITF DDAVMHWVRQ  240
APGKGLEWVA GISSNSGYIG YADSVKGRFT ISRDNAKNSL YLQMNRLRAE DTAVYYCVKG  300
LYSNPRGGAF DIWGQGTMVT VSSASTGGGG SGGGGSGGGG SVHSSYVLTQ PPSVSVAPGQ  360
TATITCGGNN IGTKSVHWYQ QKPGQAPVLV VYADSDRPSG IPERVSGSNS GNTATLTISR  420
VEAGDEADYY CQVWDSRSDH LWVFGGGTKL TVLGGGGGSG GGGSGGGGSG GGGSGGGGSI  480
WELKKDVYVV ELDWYPDAPG EMVVLTCDTP EEDGITWTLD QSSEVLGSGK TLTIQVKEFG  540
DAGQYTCHKG GEVLSHSLLL LHKKEDGIWS TDILKDQKEP KNKTFLRCEA KNYSGRFTCW  600
WLTTISTDLT FSVKSSRGSS DPQGVTCGAA TLSAERVRGD NKEYEYSVEC QEDSACPAAE  660
ESLPIEVMVD AVHKLKYENY TSSFFIRDII KPDPPKNLQL KPLKNSRQVE VSWEYPDTWS  720
TPHSYFSLTF CVQVQGKSKR EKKDRVFTDK TSATVICRKN ASISVRAQDR YYSSSWSEWA  780
SVPCSGGGGG GSRNLPVATP DPGMFPCLHH SQNLLRAVSN MLQKARQTLE FYPCTSEEID  840
HEDITKDKTS TVEACLPLEL TKNESCLNSR ETSFITNGSC LASRKTSFMM ALCLSSIYED  900
LKMYQVEFKT MNAKLLMDPK RQIFLDQNML AVIDELMQAL NFNSETVPQK SSLEEPDFYK  960
TKIKLCILLH AFRIRAVTID RVTSYLNAS                                    989
```

INTERLEUKIN 18 (IL-18) VARIANTS AND FUSION PROTEINS COMPRISING SAME

CROSS-REFERENCE TO RELATED APPLICATIONS

This application claims priority under 35 U.S.C. § 119 (e) to U.S. Provisional Patent Application No. 63/658,322 filed Jun. 10, 2024, and U.S. Provisional Patent Application No. 63/616,148 filed Dec. 29, 2023, which are herein incorporated by reference in their entirety for all purposes.

SEQUENCE LISTING

The instant application contains a Sequence Listing which has been submitted electronically in XML format and is hereby incorporated by reference in its entirety. Said XML copy, created on Jun. 12, 2024, is named 116076-5021-US.xml and is 40000 bytes in size.

FIELD

The disclosure generally relates to variant interleukin-18 proteins (e.g., variant human IL-18 proteins) and fusion proteins comprising the variant interleukin-18 proteins.

BACKGROUND

Interleukin-18 (IL-18) is an immunostimulatory cytokine belonging to the IL-1 family. IL-18 can regulate both innate and adaptive immune responses through its effects on natural killer (NK) cells, monocytes, dendritic cells, T cells, and B cells. IL-18 acts synergistically with other pro-inflammatory cytokines to promote interferon-γ (IFN-γ) production by NK cells and T cells. Systemic administration of IL-18 has been shown to have anti-tumor activity in several animal models. Moreover, tumor-infiltrating lymphocytes (TILs) express more IL-18 receptors than other T cells. However, IL-18 clinical trials show that while it was well tolerated, it had poor efficacy in the treatment of cancers. Such poor efficacy is due in part to the high co-expression of IL-18 binding protein (IL-18BP) in the tumor microenvironment. In particular, IL-18BP serves as a "decoy receptor" that binds to IL-18 with nearly 100-fold higher affinity compared with the IL18-IL18Rc complex, thereby causing a negative feedback loop with IL-18 and inhibiting IL-18 mediated TIL activation. Thus, there remains a need for IL-18 variant compositions for the treatment of cancers.

SUMMARY

Provided herein are variant human IL-18 (hIL-18) polypeptides or proteins, and related fusion proteins. Such variant hIL-18 polypeptides or proteins may be capable of wild-type IL-18 activity while having reduced or no detectable binding to inhibitory IL-18BP. Thus, in embodiments, the variant hIL-18 polypeptides or proteins advantageously retain IL-18 activity in the presence of IL-18BP. Accordingly, such variant hIL-18 polypeptides, proteins, and related fusion proteins find use, for example, in the treatment of cancers.

In a first aspect, provided herein is a variant human IL-18 (hIL-18) polypeptide or protein comprising a substitution at one or more of the following amino acid positions: Y1, M51, M60, S105, and/or D110, as compared to human wild-type IL-18 (SEQ ID NO:2).

In some embodiments, the substitution is selected from one or more of the following: Y1W, Y1K, M51Y, M51S, M60W, S105E, and D110Y. In certain embodiments, the variant hIL-18 polypeptide or protein comprises the following substitutions: Y1W, M51Y, M60W, and D110Y. In other embodiments, the variant hIL-18 polypeptide or protein comprises the following substitutions: Y1K, M51S, M60W, S105E, and D110Y.

In some embodiments, the variant hIL-18 polypeptide or protein further comprises one or more of the following amino acid substitutions: C38S, C68S, C76S, C127S. In certain embodiments, the variant hIL-18 polypeptide or protein further comprises one or more of the following amino acid substitutions: C38S, C68S, C76S, and/or C127S.

In some embodiments, the variant hIL-18 polypeptide or protein comprises the following amino acid substitutions: Y1W, C38S, M51Y, M60W, C68S, C76S, D110Y, and C127S, as compared to human wild-type IL-18 (SEQ ID NO:2). In some embodiments, the variant hIL-18 polypeptide or protein comprises an amino acid sequence as set forth in SEQ ID NO:3.

In some embodiments, the variant hIL-18 polypeptide or protein comprises the following amino acid substitutions: Y1K, C38S, M51S, M60W, C68S, C76S, S105E, D110Y, C127S, as compared to human wild-type IL-18 (SEQ ID NO:2). In exemplary embodiments, the variant hIL-18 polypeptide or protein comprises an amino acid sequence as set forth in SEQ ID NO:4.

In some embodiments, the variant hIL-18 polypeptide or protein exhibits reduced or no detectable binding to IL-18 binding protein as compared to wild-type hIL-18 (SEQ ID NO:2). In exemplary embodiments, the variant hIL-18 polypeptide or protein has increased IL-18 activity in the presence of IL-18 binding protein, as compared to wild-type hIL-18 (SEQ ID NO:2).

In another aspect, provided herein is a variant human IL-18 (hIL-18) fusion protein comprising a variant hIL-18 polypeptide or protein attached to (e.g., linked to) a human albumin binding domain (ABD), wherein the ABD comprises an antibody heavy chain variable domain (VH), and an antibody light chain variable domain (VL).

In some embodiments, the VH comprises an amino acid sequence of SEQ ID NO:5, and the VL comprises an amino acid sequence of SEQ ID NO:9.

In some embodiments, the variant hIL-18 polypeptide or protein comprises a substitution at one or more of the following amino acid positions Y1, M51, M60, S105, and/or D110, as compared to human wild-type IL-18 (SEQ ID NO:2). In some embodiments, the substitution is selected from one or more of the following: Y1W, Y1K, M51Y, M51S, M60W, S105E, and/or D110Y. In some embodiments, the variant hIL-18 polypeptide or protein comprises the following substitutions: Y1W, M51Y, M60W, and D110Y. In some embodiments, the variant hIL-18 polypeptide or protein comprises the following substitutions: Y1K, M51S, M60W, S105E, and D110Y. In some embodiments, the variant hIL-18 polypeptide or protein further comprises one or more of the following amino acid substitutions: C38S, C68S, C76S, and/or C127S. In some embodiments, the variant hIL-18 further comprises C38S, C68S, C76S, and C127S amino acid substitutions.

In exemplary embodiments, the variant hIL-18 polypeptide or protein comprises the following amino acid substitutions: Y1W, C38S, M51Y, M60W, C68S, C76S, D110Y, and C127S. In some embodiments, the variant hIL-18 polypeptide or protein comprises an amino acid sequence as set forth in SEQ ID NO:3.

In some embodiments, the variant hIL-18 polypeptide or protein comprises the following amino acid substitutions: Y1K, C38S, M51S, M60W, C68S, C76S, S105E, D110Y, and C127S. In some embodiments, the variant hIL-18 polypeptide or protein comprises an amino acid sequence as set forth in SEQ ID NO:4.

In exemplary embodiments, the human albumin binding domain is an scFv, and the VH is attached to the VL by an scFv linker. In some embodiments, the variant hIL-18 polypeptide or protein is operable linked to the human albumin binding domain by a peptide linker.

In some embodiments, the variant hIL-18 polypeptide or protein exhibits reduced or no detectable binding to IL-18 binding protein as compared to wild-type hIL-18 (SEQ ID NO:2). In exemplary embodiments, the variant hIL-18 polypeptide or protein has increased IL-18 activity in the presence of IL-18 binding protein, as compared to wild-type hIL-18 (SEQ ID NO:2).

In another aspect, provided herein is an IL-18/IL-12 albumin binding domain fusion protein comprising: a) a human IL-18 (hIL-18) polypeptide or protein; b) a human IL-12 (hIL-12) polypeptide or protein; and c) a human albumin binding domain (hABD), wherein the human albumin binding domain is an scFv that comprises an antibody heavy chain variable domain (VH), an antibody light chain variable domain (VL), and an scFv linker that attached the VH and VL, and wherein the hIL-18 polypeptide or protein is attached to the human albumin binding domain by a first peptide linker, and the hIL-12 is attached to the human albumin binding domain by a second peptide linker.

In some embodiments, the IL-18/IL-12 albumin binding domain fusion protein comprises from N- to C-terminus: hIL-18-linker 1-hABD-linker 2-hIL-12. In other embodiments, the IL-18/IL-12 albumin binding domain fusion protein comprises from N- to C-terminus: hIL-12-linker 2-hABD-linker 1-hIL18.

In some embodiments, the VH comprises an amino acid sequence as set forth in SEQ ID NO: 5, and the VL comprises an amino acid sequence as set forth in SEQ ID NO:9.

In some embodiments, the variant hIL-18 polypeptide or protein comprises a substitution at one or more of the following amino acid positions: Y1, M51, M60, S105, D110, as compared to human wild-type IL-18 (SEQ ID NO:2). In some embodiments, the substitution is selected from one or more of the following: Y1W, Y1K, M51Y, M51S, M60W, S105E, and D110Y. In some embodiments, the variant hIL-18 polypeptide or protein comprises the following substitutions: Y1W, M51Y, M60W, and D110Y. In some embodiments, the variant hIL-18 polypeptide or protein comprises the following substitutions: Y1K, M51S, M60W, S105E, and D110Y. In some embodiments, the variant hIL-18 polypeptide or protein further comprises one or more of the following amino acid substitutions: C38S, C68S, C76S, and/or C127S. In some embodiments, the variant hIL-18 polypeptide or protein further comprises C38S, C68S, C76S, and C127S.

In exemplary embodiments, the variant hIL-18 polypeptide or protein comprises the following amino acid substitutions: Y1W, C38S, M51Y, M60W, C68S, C76S, D110Y, and C127S, as compared to human wild-type IL-18 (SEQ ID NO:2). In some embodiments, the variant hIL-18 polypeptide or protein comprises an amino acid sequence as set forth in SEQ ID NO:3.

In some embodiments, the variant hIL-18 polypeptide or protein comprises the following amino acid substitutions: Y1K, C38S, M51S, M60W, C68S, C76S, S105E, D110Y, and C127S, as compared to human wild-type IL-18 (SEQ ID NO:2). In some embodiments, the variant hIL-18 polypeptide or protein comprises an amino acid sequence as set forth in SEQ ID NO:4.

In exemplary embodiments, the human albumin binding domain is an scFv, and the VH is attached to the VL by an scFv linker. In some embodiments, the variant hIL-18 polypeptide or protein is operable linked to the human albumin binding domain by a peptide linker.

In some embodiments, the hIL-12 polypeptide or protein has the amino acid sequence as set forth in SEQ ID NO:14.

In some embodiments, the variant hIL-18 polypeptide or protein exhibits reduced or no detectable binding to IL-18 binding protein as compared to wild-type hIL-18 (SEQ ID NO:2). In exemplary embodiments, the variant hIL-18 polypeptide or protein has increased IL-18 activity in the presence of IL-18 binding protein, as compared to wild-type hIL-18 (SEQ ID NO:2).

In another aspect, provided herein are nucleic acids and expression vectors that encode for the variant human IL-18 polypeptides, proteins, or fusion proteins as disclosed herein, host cells that include the nucleic acids and expression vectors as disclosed herein, and methods of making the variant human IL-18 polypeptides, proteins, or fusion proteins as disclosed herein.

In yet another aspect, provide herein are methods of treating a cancer in a patient comprising administering to the patient a variant human IL-18 polypeptide, protein, or fusion protein as provided herein.

BRIEF DESCRIPTION OF THE DRAWINGS

The foregoing summary, as well as the following detailed description, will be better understood when read in conjunction with the appended figures. For the purpose of illustration, shown in the figures are embodiments. It should be understood, however, that the summary, detailed description, and figures are not limited to the precise arrangements, examples and instrumentalities shown.

FIG. 1 depicts IL-18 amino acid sequences, including mature wild-type human IL-18 (SEQ ID NO:2), and exemplary variant human IL-18 amino acid sequences (SEQ ID NO:3 and SEQ ID NO:4).

FIG. 2 depicts an exemplary albumin binding domain (ABD) that is useful in the subject IL-18/albumin binding domain (ABD) fusion proteins provided herein.

FIG. 3 depicts the sequence of an exemplary human single chain IL-12 that is included in embodiments of the subject IL-18/IL-12 ABD fusion protein provided herein.

FIG. 4 depicts linkers useful for attaching components of the IL-18 fusion proteins, ABDs, and IL-12 constructs described herein.

FIG. 5 depicts several exemplary IL-18/ABD fusion proteins provided herein.

FIGS. 6A-B depict several exemplary (FIG. 6A) and variant (FIG. 6B) IL-18/IL-12 ABD fusion proteins provided herein.

FIG. 7 depicts a summary of a study to assess the IL-18 activity of exemplary IL-18/IL-12 ABD fusion proteins provided herein in the absence of IL-18 binding protein by HEK-Blue™ Reporter Assay.

FIGS. 8A-C depict a summary of a study to assess the IL-18 activity of exemplary IL-18/IL-12 ABD fusion proteins of 8A) hIL18-ABD-IL12 Variant B, 8B) hIL18-ABD-IL12 Variant A, and 8C) IL-18 reference standard by Bright-Glo™ Luciferase Reporter Assay.

FIGS. 9A-C depict a summary of a study to assess the IL-18 activity of exemplary IL-18 Variant A and Variant B provided herein in the absence (FIG. 9A) and presence (FIG. 9B—Variant A; and 9C—Variant B) of IL-18 binding protein.

FIGS. 10A and B depict a summary of a study to assess the binding activity of 10A) reference IL-18 control molecule and of 10B) exemplary hIL18-ABD-IL12 Variant A provided herein to the inhibitory IL-18 binding protein.

DETAILED DESCRIPTION

A. Overview

Figure 9A:
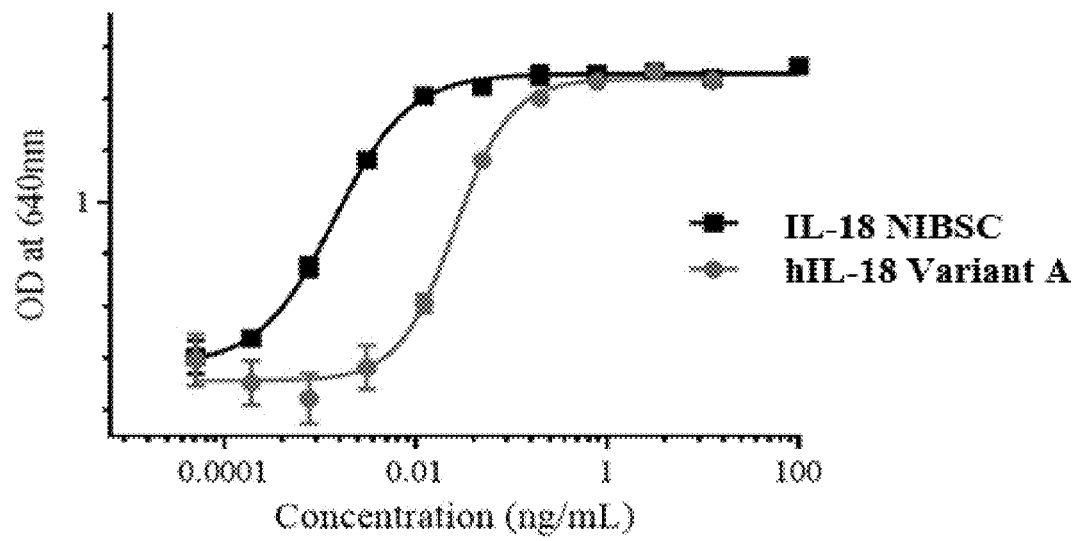

Components of the IL-18 pathway have been found to be upregulated on tumor infiltrating lymphocytes (TILs), suggesting that IL-18 could enhance anti-tumor activity. Recombinant IL-18, however, previously failed to demonstrate efficacy in clinical trials. The poor efficacy is due in part to the high co-expression of a 100-fold higher affinity IL-18 binding protein (IL-18BP) in the tumor microenvironment. In particular, IL-18BP serves as a "decoy receptor" that binds to IL-18 with higher affinity compared with the IL18-IL18Rc complex, thereby causing a negative feedback loop with IL-18 and inhibiting IL-18 mediated TIL activation.

Provided herein are variant human IL-18 (hIL-18) polypeptides or proteins that unexpectedly exhibit IL-18 activity ($EC_{50}$ values about 3 pM to about 125 pM) comparable to that of hIL-18 a reference standard while having reduced or no detectable binding to inhibitory IL-18BP. Thus, in embodiments, the variant hIL-18 polypeptides or proteins retain IL-18 activity in the presence of IL-18BP. Such variant hIL-18 polypeptides or proteins find use, for example, in the treatment of cancer. Also provided herein are variant IL-18 fusion proteins that include an albumin binding domain (ABD) that increases serum half-life. In some embodiments, the variant IL-18 fusion proteins further include an IL-12 polypeptide or protein. Without being bound by any particular theory of operation, it is believed that such IL-18/IL-12 fusion proteins exhibit synergistic anti-tumor activity in comparison to either IL-18 or IL-12 alone.

Various aspects of the variant IL-18 polypeptides, proteins and fusion proteins are further detailed herein.

B. Variant IL-18 Polypeptides and Proteins

In one aspect, provided herein are variant interleukin 18 (IL-18) proteins. As used herein "interleukin-18," "interleukin 18," "IL-18," "IGIF," "IL-1g," "IL1F4," and "interferon-gamma inducing factor," all refer to a proinflammatory cytokine that is part of the IL-1 superfamily and is encoded by the IL18 gene in humans. IL-18 is produced as a biologically inactive 193 amino acid precursor (SEQ ID NO:1), which is capable of being processed intracellularly by caspase 1 into biologically active mature IL-18 (SEQ ID NO:2). Mature IL-18 binds to a receptor complex that is highly expressed on NK cells and is composed of at least two subunits, IL-18Rα (IL-1Rrp1) and IL-18Rβ (AcPL). In addition to its ability to directly promote the proliferation and migration of cells in certain types of cancer, tumor-infiltrating NK cells and CD8+ T cells express high levels of IL-18.

As used throughout this disclosure, the phrase "as compared to human wild-type IL-18" or "relative to human wild-type IL-18," when referring to an amino acid modification (e.g., an amino acid substitution) in a variant IL-18 protein, refers to the corresponding amino acid position in human wild-type IL-18 (SEQ ID NO:2). For example, a Y1 amino acid substitution in a variant IL-18 protein, as disclosed herein, is at an amino acid position in the variant IL-18 protein that corresponds to Y1 of human wild-type IL-18 (SEQ ID NO:2).

In some embodiments, the variant IL-18 protein (e.g, variant IL-18 mature protein or variant IL-18 pre-protein) comprises one or more of the amino acid substitutions as set forth in Table 1. The substitutions in the variant IL-18 protein correspond to those amino acid positions in the IL-18 mature protein (SEQ ID NO: 2) or IL-18 pre-protein (SEQ ID NO: 1) set forth in Table 1. In a further embodiment, an IL-18 variant ("Variant A") is provided that comprises or consists of eight amino acid substitutions as set forth in Table 1. In another embodiment, an IL-18 variant ("Variant B") is provided that comprises or consists of nine amino acid substitutions as set forth in Table 1.

TABLE 1

Exemplary IL-18 Amino Acid Substitutions

| Position in IL-18 mature protein | Position in IL-18 pre-protein | Substitutions in Variant A | Substitutions in Variant B |
|---|---|---|---|
| 1 | 37 | W | K |
| 38 | 74 | S | S |
| 51 | 87 | Y | S |
| 60 | 96 | W | W |
| 68 | 104 | S | S |
| 76 | 112 | S | S |
| 105 | 141 | — | E |
| 110 | 146 | Y | Y |
| 127 | 163 | S | S |

In some embodiments, the variant IL-18 protein is a variant of a mature wild-type human IL-18 protein ("hIL-18," SEQ ID NO:2). In some embodiments, the variant human IL-18 protein provided herein advantageously exhibits reduced or no detectable binding to inhibitory IL-18 binding protein (IL-18BP) as compared to wild-type IL-18 protein. In some embodiments, the variant hIL-18 protein is capable of binding to and activating signaling via the IL-18 receptor. Thus, while not being bound by any particular theory of operation, it is believed that, in some embodiments, the variant IL-18 protein exhibits greater IL-18 activity in comparison to wild-type IL-18 protein in the presence of IL-18BP. In some embodiments, the variant hIL-18 protein provided herein are is useful as a therapy for the treatment of cancer.

In some embodiments, the variant hIL-18 protein includes one or more amino acid substitutions that reduce binding to IL-18BP. Amino acid positions in hIL-18 that can be substituted to decrease binding to IL-18BP include, but are not limited to: Y1, M51, M60, S105, and/or D110, wherein the numbering is in reference to mature human IL-18 protein (SEQ ID NO:2, FIG. 1).

In some embodiments, the variant hIL-18 protein is substituted at 1, 2, 3, 4 or all of the following positions: Y1, M51, M60, S105, and/or D110 of wild-type human IL-18 protein (SEQ ID NO: 2). In some embodiments, the variant hIL-18 protein includes one or more of the following amino acid substitutions as compared to SEQ ID NO:2: Y1W, Y1K, M51Y, M51S, M60W, S105E, and/or D110Y. In some embodiments, the variant hIL-18 protein includes a Y1W or Y1K amino acid substitution. In certain embodiments, the variant hIL-18 protein includes a M51Y or M51S amino acid substitution. In some embodiments, the variant hIL-18 protein includes an M60W amino acid substitution. In certain embodiments, the variant hIL-18 protein includes a S105E amino acid substitution. In some embodiments, the variant hIL-18 protein includes a D110Y amino acid substitution. In exemplary embodiments, the variant hIL-18 protein includes the following amino acid substitutions: Y1W, M51Y, M60W, and D110Y. In some embodiments, the variant hIL-18 protein includes the following amino acid substitutions: Y1K, M51S, M60W, S105E, and D110Y.

In embodiments, the variant hIL-18 protein provided herein includes one or more amino acid substitutions of a cysteine residue(s) compared to a wild-type hIL-18 protein. IL-18 aggregation can result in inactive IL-18 aggregates that prove challenging to remove during downstream purification efforts and are unstable for clinical use. Thus, without being bound by any particular theory of operation, it is believed that such cysteine substitutions reduce intermolecular disulfide bond formation between IL-18 molecules that causes aggregation, thereby enhancing IL-18 activity. In some embodiments, one or more of the following amino acid positions is modified as compared to wild-type hIL-18 protein (SEQ ID NO:2): C38, C68, C76, and C127. In some embodiments, the amino acid substitution is a cysteine/serine substitution. In exemplary embodiments, the variant hIL-18 protein includes the following amino acid substitution(s): C38S, C68S, C76S, and/or C127S.

Exemplary variant hIL-18 proteins are depicted in FIG. 1. In some embodiments, the variant hIL-18 protein comprises the amino acid as set forth in SEQ ID NO:3 or a variant thereof that includes 1, 2, 3, 4, 5, 6, 8, 9, or 10 additional amino acid modifications (e.g, substitutions, deletions, or insertions) as compared to SEQ ID NO:2. In some embodiments, the variant hIL-18 protein comprises the amino acid as set forth in SEQ ID NO:4 or a variant thereof that includes 1, 2, 3, 4, 5, 6, 8, 9, or 10 additional amino acid modifications (e.g, substitutions, deletions, or insertions) as compared to SEQ ID NO:2.

In some embodiments, the variant IL-18 protein includes 1, 2, 3, 4, 5, 6, 7, 8, 9, 10, 11, 12, 13, 14, 15, 16, 17, 18, 19, 20, 21, 22, 23, 24, or 25 amino acid modifications (e.g, substitutions, deletions, or insertions) as compared to mature wild-type hIL-18 (SEQ ID NO:2). In some embodiments, the amino acid sequence of the variant IL-18 protein is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of mature wild-type hIL-18 protein (SEQ ID NO: 2). In some embodiments, the amino acid sequence of the variant IL-18 protein is 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of mature wild-type hIL-18 protein (SEQ ID NO: 2).

In some embodiments, the variant IL-18 protein exhibits reduced or no detectable binding to IL-18 binding protein (IL-18BP) as compared to wild-type human IL-18 protein (SEQ ID NO: 2). In some embodiments, the variant IL-18 protein exhibits enhanced IL-18 activity compared to wild-type human IL-18 protein (SEQ ID NO:2) in the presence of IL-BP. The IL-18 activity of the variant hIL-18 protein described herein can be measured using any suitable technique known in the art. In some embodiments, the IL-18 activity of the of the variant hIL-18 protein is measured using an assay that measures activation of the NF-κB and/or AP-1 pathways (e.g., a HEK-Blue™ Reporter assay or Bright-Glo™ Luciferase assay; see also Kurata et al., Mar Druges 18 (1): 60 (2020)). In some embodiments, the variant hIL-18 protein exhibits at least 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200% more activity as compared to wild-type hIL-18 protein. In exemplary embodiments, the variant hIL-18 protein exhibits at least 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200% more activity as compared to wild-type hIL-18 protein in the presence of IL-18BP.

C. IL-18/Albumin Binding Domain Fusion Proteins

In another aspect, provided herein are IL-18 fusion proteins that include an IL-18 (human IL-18, SEQ ID NO:2) or a variant IL-18 protein as disclosed herein operably linked to an albumin binding domain (ABD), i.e., an IL-18/ABD fusion protein.

Fusion proteins that include the subject albumin binding domain (ABD) can bind serum albumin (SA), which allows the fusion protein to be taken in by cells by macropinocytosis. In certain embodiments, the ABDs described herein bind to FcRn via SA at low pH (e.g., pH 5.8), which in turn diverts the SA bound ABD fusion protein from the lysosome compartment of the cell and back to the plasma membrane. At the plasma membrane, the SA dissociates from FcRn due to the neutral pH (e.g., pH 7.2) and the SA and ABD fusion protein are released back into the bloodstream. As therapeutics that include the subject ABD which are capable of binding to albumin at a pH range of about pH 5.8 to about pH 7.2, such therapeutics advantageously also undergo FcRn-driven endosomal albumin recycling and, thus, evade lysosomal degradation. Accordingly, therapeutics that include such ABDs advantageously exhibit longer serum half-lives than counterparts lacking ABDs. Such therapeutics are particular useful for the treatment of cancers, which are known to contain high levels of serum albumin.

As used herein, "serum albumin" refers to a member of a family of globular proteins produced by the liver that functions primarily as a carrier protein of steroids, fatty acids, and thyroid hormones in the blood. Serum albumin also plays a major role in stabilizing extracellular fluid volume by contributing to oncotic pressure of plasma, and includes, but is not limited to, human serum albumin (HSA, Genbank Accession numbers: NM_000477 and NP_000468) and mouse serum albumin (MSA, Genbank accession numbers: NM_009654 and NP_0033784). The structure of albumin is characterized by several long a helices and contains eleven distinct binding domains for hydrophobic compounds. In humans, serum albumin is encoded by the ALB gene.

In some embodiments, the IL-18/ABD fusion protein binds albumin at a site that does not interfere with SA binding to a neonatal Fc receptor (FcRn). By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two fusion proteins, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

In some embodiments, the IL-18/ABD fusion protein described or exemplified herein preferably specifically binds to serum albumin (e.g., human SA (HSA)) at an epitope on the serum albumin molecule that does not participate in the interaction of the serum albumin molecule with the FcRn. Binding of the SA binding moiety to the serum albumin molecule thus preferably does not substantially interfere with, inhibit, prevent, or otherwise reduce binding of the serum albumin molecule (e.g., HSA) with the FcRn. Preferably, the IL-18/ABD fusion protein does not compete with the FcRn for binding to the serum albumin molecule. Preferably, the IL-18/ABD fusion protein does not sterically inhibit binding of serum albumin to the FcRn. Preferably, the IL-18/ABD fusion protein does not change the conformation of the serum albumin molecule such that the albumin cannot interact with the FcRn.

In some embodiments, the IL-18/ABD fusion protein binds SA (e.g., HSA) at a pH of 5.0±0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0. 2.1, 2.2, 2.3, 2.4, 2.5, 2.6, 2.7, 2.8, 2.9, or 3.0. In some embodiments, the IL-18/ABD fusion protein binds SA at a range of pH of about pH 5.8 to about pH 7.2.

In certain embodiments, the albumin binding domain of the IL-18/ABD fusion protein is a human serum albumin (HSA) binding domain. HSA binding domains include, but are not limited to, albumin binding domains that can bind to an HSA molecule such as a whole HSA molecule or a fragment of an HSA. In some embodiments, the HSA binding domain also binds mouse serum albumin. In some embodiments, the HSA binding domain also binds cyno monkey albumin. In certain embodiments, the HSA binding domain does not bind to bovine serum albumin (BSA).

Albumin binding domains provided herein can include a variable heavy chain alone or a variable heavy chain in association with a variable light chain. In some embodiments, the albumin binding domain includes a variable heavy chain. In certain embodiments, the variable heavy chain includes a vhCDR1, vhCDR2, and vhCDR3 (variable heavy chain Complementary Determining Regions 1-3). In certain embodiments, the antigen binding domain also includes a variable light chain. In certain embodiments, the variable light chain includes a vlCDR1, vlCDR2 and vlCDR3 (variable light chain Complementary Determining Regions 1-3).

In certain embodiments, the albumin binding domain (e.g., HSA binding domain) is an antibody or an antibody fragment. In some embodiments, the albumin binding domain (e.g., HSA binding domain) is an scFv.

In some embodiments where the ABD includes both a variable heavy chain and a variable light chain, the variable heavy chain and the variable light chain are attached to each other by a linker (e.g., an scFv linker). In certain embodiments, the linker is attached to the variable heavy chain at its C-terminus and the variable light chain at its N-terminus. Suitable linkers are described herein and in FIG. 4. In some embodiments, the linker is a (Gly4Ser)$_x$ linker, where x is 1, 2, 3, 4, 5, 6, 7, or 8. In certain embodiments, the linker is a (Gly4Ser)$_3$ linker (SEQ ID NO:17).

In certain embodiments, the albumin binding domain also includes a variable heavy chain that includes the vhCDR1, vhCDR2 and vhCDR3 of A10m3 and a variable light chain that includes the vlCDR1, VlCDR2 and vlCDR3 of A10m3 (FIG. 2). In some embodiments, the albumin binding domain includes the variable heavy sequence and variable light sequence of the A10m3 ABD depicted in FIG. 2 (SEQ ID NO:5 and SEQ ID NO:9, respectively). In some embodiments, the ABD is an scFv that has the amino acid sequence of SEQ ID NO:13.

In some embodiments, the IL-18/ABD fusion protein includes an albumin binding domain that is a variant of the A10m3 albumin binding domain depicted in FIG. 2. In some embodiments, the variant VH domain and/or VL domain has from 1, 2, 3, 4, 5, 6, 7, 8, 9 or 10 amino acid modifications from a VH and/or VL domain of the A10m3 albumin binding domain (FIG. 2). In some embodiments, the amino acid modifications are in a VH domain according to SEQ ID NO:5. In some embodiments, the amino acid modifications are in a VL domain according to SEQ ID NO: 9. In some embodiments, the one or more amino acid modifications are in the VH and/or VL framework regions (FR1, FR2, FR3, and/or FR4). In some embodiments, the one or more amino acid modifications are in one or more CDRs. In certain embodiments, the ABD of the IL-18/ABD fusion protein is capable of binding to serum albumin, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the ABD of the IL-18/ABD fusion protein is capable of binding human albumin.

In one embodiment, the variant VH and/or VL domain is at least 90, 95, 97, 98 or 99% identical to the VH and/or VL of the A10m3 albumin binding domain depicted in FIG. 2. In some embodiments, the ABD includes a VH that is at least 90, 95, 97, 98 or 99% identical to the VH domain according to SEQ ID NO:5. In some embodiments, the ABD includes a VL that is at least 90, 95, 97, 98 or 99% identical to the VL domain according to SEQ ID NO:9. In some embodiments, the ABD includes a VH and a VL that is at least 90, 95, 97, 98 or 99% identical to the VH domain and the VL domain according to SEQ ID NOs: 5 and 9, respectively. In certain embodiments, the ABD of the IL-18/ABD fusion protein is capable of binding to serum albumin, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the ABD of the IL-18/ABD fusion protein is capable of binding human albumin.

Any suitable IL-18 protein can be included in the IL-18/ABD fusion protein, including any of the variant IL-18 proteins described herein. In some embodiments, the IL-18 protein is human IL-18 (SEQ ID NO:2). In some embodiments, the IL-18 protein is a variant human IL-18 protein.

In some embodiments, the variant hIL-18 protein of the IL-18/ABD fusion protein is modified at 1, 2, 3, 4 or all of the following positions: Y1, M51, M60, S105, D110 of wild-type human IL-18 (SEQ ID NO:2). In some embodiments, the variant hIL-18 includes one or more of the following amino acid substitutions as compared to SEQ ID NO:2: Y1W, Y1K, M51Y, M51S, M60W S105E, and/or D110Y. In some embodiments, the variant hIL-18 protein of the IL-18/ABD fusion protein includes a Y1W or Y1K amino acid substitution. In certain embodiments, the variant hIL-18 protein includes a M51Y or M51S amino acid substitution. In some embodiments, the variant hIL-18 protein includes an M60W amino acid substitution. In certain embodiments, the variant hIL-18 protein includes a S105E amino acid substitution. In some embodiments, the variant hIL-18 protein includes a D110Y amino acid substitution. In exemplary embodiments, the variant hIL-18 protein includes the following amino acid substitutions: Y1W, M51Y, M60W, and D110Y. In some embodiments, the variant hIL-18 protein includes the following amino acid substitutions: Y1K, M51S, M60W, S105E, and D110Y.

In embodiments, the variant hIL-18 protein of the IL-18/ABD fusion protein includes one or more amino acid substitutions, wherein a cysteine of a wild-type hIL-18 protein is modified to reduce protein aggregation. In some embodiments, one or more of the following amino acid positions is modified (e.g, substituted) as compared to wild-type hIL-18 (SEQ ID NO:2): C38, C68, C76, and C127. In some embodiments, the amino acid modification is a cysteine/serine substitution. In exemplary embodiments, the variant hIL-18 protein of the IL-18/ABD fusion protein includes the following amino acid substitution(s): C38S, C68S, C76S, and/or C127S. In exemplary embodiments, the variant hIL-18 protein of the IL-18/ABD fusion protein i comprises the amino acid sequence as set forth in SEQ ID NO:3 or SEQ ID NO:4, or a variant thereof.

Any suitable linker can be used to link the IL-18 protein to the albumin binding domain of the IL-18/ABD fusion protein. Suitable linkers for attaching the IL-18 protein and albumin binding domain peptide liners as shown, for example, in FIG. 4. As shown herein, there are a number of suitable linkers that can be used, including traditional peptide bonds, generated by recombinant techniques. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n, (GGGGS)n, and (GGGS)n, where n is an integer of at least one (and generally from 3 to 5), glycine-alanine polymers, alanine-serine polymers, and other flexible linkers. Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers, that is may find use as linkers. In some embodiments the linker is a (Gly4Ser)$_5$ linker (SEQ ID NO:19).

Exemplary IL-18/ABD fusion proteins are depicted in FIG. 5.

1. IL-18/IL-12 Albumin Binding Domain Fusion Proteins

In another aspect, provided herein are IL-18/IL-12 albumin binding domain (ABD) fusion proteins that include an IL-18 protein, an IL-12 protein, and an albumin binding domain.

IL-18 is capable of inducing IFN-γ production, and promoting Th1 cell development and NK activation. IL-12 is capable of inducing the upregulation of the IL-18 receptor in an IFN-γ-dependent manner. IL-18 and IL-12 are also capable of synergistically inducing prolonged serum levels of IFN-γ. Moreover, IL-18 can increase CXCL9 and CXCL10 expression, which have been shown to associate with levels of TIL infiltrate in human cancers, and improved responses to chemotherapy and adoptive cellular therapy. Thus, without being bound by any particular theory of operation, it is believed that fusion proteins that include a variant IL-18 and IL-12 are capable of synergistic anti-tumor activity in comparison to IL-18 or IL-12 alone.

In some embodiments, the IL-18/IL-12 ABD fusion protein is according to the formula, from N- to C-terminus: IL-18-linker-ABD-linker-IL12. In some embodiments, the IL-18/IL-12 ABD fusion protein is according to the formula, from N- to C-terminus: IL-12-linker-ABD-linker-IL18.

Any suitable IL-18 protein and albumin binding domain can be included in the subject IL-18/IL-12 albumin binding domain (ABD) fusion protein. In some embodiments, the IL-18 protein is a human IL-18 protein. In some embodiments the IL-18 protein is a variant of a human IL-18 protein (SEQ ID NO:2). In exemplary embodiments, the variant hIL-18 protein exhibits enhanced IL-18 activity as compared to wild-type IL18 in the presence of IL-18 binding protein (IL-18BP). In some embodiments, the variant hIL-18 protein includes one or more of the following amino acid substitutions as compared to SEQ ID NO:2: Y1W, Y1K, M51Y, M51S, M60W, S105E, and/or D110Y. In some embodiments, the variant hIL-18 protein of the IL-18/IL-12 ABD fusion protein includes a Y1W or Y1K amino acid substitution. In certain embodiments, the variant hIL-18 protein includes a M51Y or M51S amino acid substitution. In some embodiments, the variant hIL-18 protein includes an M60W amino acid substitution. In certain embodiments, the variant hIL-18 protein includes a S105E amino acid substitution. In some embodiments, the variant hIL-18 protein includes a D110Y amino acid substitution. In exemplary embodiments, the variant hIL-18 protein includes the following amino acid substitutions: Y1W, M51Y, M60W, and D110Y. In some embodiments, the variant hIL-18 protein includes the following amino acid substitutions: Y1K, M51S, M60W, S105E, and D110Y.

In embodiments, the variant hIL-18 protein of the IL-18/IL-12 ABD fusion protein includes one or more amino acid substitutions, wherein a cysteine of a wild-type hIL-18 protein is modified. In some embodiments, one or more of the following amino acid positions is modified as compared to wild-type hIL-18 protein (SEQ ID NO:2): C38, C68, C76, and C127. In some embodiments, the amino acid modification is a cysteine/serine substitution. In exemplary embodiments, the variant hIL-18 protein of the IL-18/ABD fusion protein includes the following amino acid substitution(s): C38S, C68S, C76S, and/or C127S. In exemplary embodiments, the variant hIL-18 protein of the IL-18/ABD fusion protein comprises an amino acid sequence as set forth in SEQ ID NO:3 or SEQ ID NO: 4, or a variant thereof.

The IL-18/IL-12 ABD fusion protein includes an albumin binding domain (ABD) that enhances the half-life of the fusion protein. In some embodiments, the IL-18/ABD fusion protein includes an ABD provided herein. In some embodiments, the ABD includes a VH and VL that is at least 95% identical to the amino acid sequences of the A10m3 VH and VL (SEQ ID NO:5 and SEQ ID NO:9 respectively). In some embodiments, the IL-18/IL-12 ABD fusion protein includes an ABD that includes the VH and VL sequence of the A10m3 ABD (SEQ ID NO:5 and SEQ ID NO: 9 respectively). In some embodiments, the ABD has the amino acid sequence of SEQ ID NO: 13.

The IL-18/IL-12 ABD fusion protein provided herein further includes an IL-12 protein that is linked to the ABD. As used herein, "interleukin 12," "IL-12," and "IL12" all refer to an interleukin that is a heterodimeric cytokine encoded by the IL-12A and IL-12B genes (GenBank Accession numbers: NM_000882 (IL-12A) and NM_002187 (IL-12B)). IL-12 is composed of a bundle of four alpha helices and is involved in the differentiation of native T cells into THI cells. IL-12 binds to the IL-12 receptor, which is a heterodimeric receptor formed by IL-12R-β1 and IL-12R-β2. IL-12 is known as a T cell-stimulating factor that can stimulate the growth and function of T cells. In particular, IL-12 can stimulate the production of interferon gamma (IFN-γ), and tumor necrosis factor-alpha (TNF-α) from T cells and natural killer (NK) cells and reduce IL-4 mediated suppression of IFN-γ. IL-12 can further mediate enhancement of the cytotoxic activity of NK cells and CD8+ cytotoxic T lymphocytes. Moreover, IL-12 can also have anti-angiogenic activity by increasing production of interferon gamma, which in turn increases the production of the chemokine inducible protein-10 (IP-10 or CXCL10). IP-10 then mediates this anti-angiogenic effect. Without being bound by any particular theory of operation, it is believed that IL-12 through its ability to induce immune responses and its anti-angiogenic activity can be used to treat cancers.

In some embodiments, the IL-12 protein is a human IL-12 protein. In certain embodiments, the IL-12 is a single chain IL-12 polypeptide comprising an IL-12 p35 subunit attached to an IL-12 p40 subunit. Such IL-12 single chain polypeptides advantageously retain one or more of the biological activities of wildtype IL-12. In some embodiments, the single chain IL-12 polypeptide described herein is according to the formula, from N-terminus to C-terminus, (p40)-(L)-(p35), wherein "p40" is an IL-12 p40 subunit, "p35" is IL-12 p35 subunit and L is a linker. In other embodiments, the single chain IL-12 is according to the formula from N-terminus to C-terminus, (p35)-(L)-(p40). Any suitable linker can be used in the single chain IL-12 polypeptide including those described herein and disclosed in FIG. 4. Suitable linkers can include, for example, linkers having the amino acid sequence (GGGGS)$_x$ wherein x is an integer from 1-10. Other suitable linkers include, for example, the amino acid sequence GGGGGGS. Exemplary single chain IL-12 linkers than can be used with the subject single chain IL-12 polypeptides are also described in Lieschke et al., *Nature Biotechnology* 15:35-40 (1997), which is incorporated herein in its entirety by reference and particularly for its teaching of IL-12 polypeptide linkers.

In an exemplary embodiment, the single chain IL-12 polypeptide is a single chain human IL-12 polypeptide (i.e., it includes a human p35 and p40 IL-12 subunit). Exemplary single chain human IL-12 are depicted in FIG. 3 (SEQ ID NO:14).

In embodiments of the IL-18/IL-12 ABD fusion protein, the IL-18 and IL-12 are both attached to the ABD by linkers. Any suitable linker can be used to link the IL-18 and IL-12 to the albumin binding domain of the IL-18/IL-12 ABD fusion protein, including any of the linkers described. Suitable linkers for attaching the IL-18 and albumin binding domain peptide liners as shown, for example, in FIG. 4. In some embodiments the linker is a (Gly4Ser) s linker (SEQ ID NO: 19).

Exemplary IL-18/IL-12 ABD fusion proteins are depicted in FIGS. 6A and 6B. In some embodiments, the IL-18/IL-12 ABD fusion protein has the amino acid sequence of any one of SEQ ID NOs: 32-35.

D. Production of Variant IL-18 Protein and Fusion Proteins

As will be appreciated by those in the art, standard protocols are used to make the variant IL-18 proteins or fusion protein as disclosed herein.

In one embodiment disclosed herein, nucleic acids are created that encode the variant IL-18 protein or fusion protein, and that may then be cloned into host cells, expressed and assayed, if desired. These practices are carried out using well-known procedures. For example, a variety of methods that may find use in generating the variant IL-18 proteins and fusion proteins disclosed herein are described in Molecular Cloning—A Laboratory Manual, 3rd Ed. (Maniatis, Cold Spring Harbor Laboratory Press, New York, 2001), and Current Protocols in Molecular Biology (John Wiley & Sons), both incorporated entirely by reference. There are a variety of techniques that may be used to efficiently generate DNA encoding variant IL-18 proteins and fusion proteins disclosed herein. Such methods include, but are not limited to, gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode variant IL-18 proteins and fusion proteins.

The variant IL-18 proteins or fusion proteins may be produced by culturing a host cell transformed with nucleic acid, e.g., an expression vector, containing nucleic acid encoding a variant IL-18 or fusion protein, under the appropriate conditions to induce or cause expression of the protein. The conditions appropriate for expression will vary with the choice of the expression vector and the host cell. A wide variety of appropriate host cells may be used, including but not limited to mammalian cells, bacteria, insect cells, yeast, and plant cells. For example, a variety of cell lines that may find use in generating variant IL-18 proteins and fusion proteins are described in the ATCC® cell line catalog, available from the American Type Culture Collection.

In one embodiment, the variant IL-18 proteins and fusion proteins are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternate embodiment, library proteins are expressed in bacterial cells. Bacterial expression systems are well known in the art, and include *Escherichia coli* (*E. coli*), *Bacillus subtilis, Streptococcus cremoris*, and *Streptococcus lividans*. In alternate embodiments, the variant IL-18 proteins and fusion proteins are produced in insect cells (e.g., Sf21/Sf9, *Trichoplusia ni* BTI-Tn-5B1-4) or yeast cells (e.g., *S. cerevisiae, Pichia*, etc.). In an alternate embodiment, the variant IL-18 proteins and fusion proteins are expressed in vitro using cell free translation systems. In vitro translation systems derived from both prokaryotic (e.g., *E. coli*) and eukaryotic (e.g., wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the subject variant IL-18s and fusion proteins may be produced by chemical synthesis methods. Also, transgenic expression systems including both animal (e.g., cow, sheep or goat milk, embryonated hen's eggs, whole insect larvae, etc.) and plant (e.g., corn, tobacco, duckweed, etc.) may be used for production.

The nucleic acids that encode the subject IL-18 proteins and fusion proteins may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus, expression vectors which find use in generating antibodies disclosed herein include, but are not limited to, those which enable protein expression in mammalian cells, bacteria, insect cells, yeast, and in in vitro systems. As is known in the art, a variety of expression vectors are available, commercially or otherwise, that may find use for expressing antibodies or fusion proteins disclosed herein.

The disclosed variant IL-18 proteins and fusion proteins can be encoded by multiple nucleic acid molecules. For example, the variable heavy and light chains can be introduced into a host cell independently. Though present on separate nucleic acids, their expression yields a single polypeptide.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the variant IL-18 proteins and fusion proteins, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

In one embodiment, variant IL-18 proteins and fusion proteins are purified or isolated after expression. Variant IL-18 proteins and fusion proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, isoelectric focusing, immunological, precipitation, dialysis, and chromatofocusing techniques. Ultrafiltration and diafiltration techniques, in conjunction with protein concentration, are also useful. If fusion is employed, Ni 2 affinity chromatography may be used if a His-tag is employed, or an immobilized anti-flag antibody may be used if a flag-tag is used. For general guidance in suitable purification techniques, see, e.g., incorporated entirely by reference Protein Purification: Principles and Practice, 3rd Ed., Scopes, Springer-Verlag, NY, 1994, incorporated entirely by reference. The degree of purification necessary will vary depending on the screen or use of the antibodies. In some instances no purification is needed.

E. Therapeutic Uses of Albumin Binding Domains and ABD Fusion Proteins

The variant IL-18 proteins and fusion proteins may find application in a variety of therapeutic uses as described herein.

In one aspect, provided herein is a method of inhibiting tumor growth in a subject in need thereof by administering to the subject a variant IL-18 protein or IL-18 fusion protein provided herein. Also provided herein is a method of treating a subject having cancer by administering to the subject a variant IL-18 or Il-18 fusion protein provided herein.

F. Pharmaceutical Formulations, Administration and Dosing

In another aspect, provided herein is a therapeutic composition comprising any a variant IL-18 protein or IL-18 fusion protein provided herein and a carrier. Subject therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see Remington's Pharmaceutical Sciences 16th Edition, A. Osal., Ed., 1980).

1. Administrative Modalities

The subject variant IL-18, IL-18 fusion proteins, and therapeutic agents are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

2. Treatment Modalities

In the methods provided herein, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of tumor cells; (2) an increase in tumor cell death; (3) inhibition of tumor cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

An improvement in the disease may be characterized as a complete response. By "complete response" is intended an absence of clinically detectable disease with normalization of any previously abnormal radiographic studies, bone marrow, and cerebrospinal fluid (CSF) or abnormal monoclonal protein in the case of myeloma.

Such a response may persist for at least 4 to 8 weeks, or sometimes 6 to 8 weeks, following treatment according to the subject methods. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

G. Illustration of Subject Technology as Clauses

Various examples of aspects are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1: A variant human IL-18 (hIL-18) protein comprising a substitution at one or more of the following amino acid positions: Y1, M51, M60, S105, and/or D110, as compared to human wild-type IL-18 (SEQ ID NO:2).

Clause 2: The variant hIL-18 protein of Clause 1, wherein the substitutions are selected from one or more of the following: Y1W, Y1K, M51Y, M51S, M60W, S105E, and/or D110Y.

Clause 3: The variant hIL-18 protein of Clause 2, wherein the substitutions include: Y1W, M51Y, M60W, and D110Y.

Clause 4: The variant hIL-18 protein of Clause 2, wherein the substitutions include: Y1K, M51S, M60W, S105E, and D110Y.

Clause 5: The variant hIL-18 protein of any one of Clauses 1 to 4, wherein the variant hIL-18 protein further comprises one or more of the following amino acid substitutions: C38S, C68S, C76S, and/or C127S, as compared to human wild-type IL-18 (SEQ ID NO:2).

Clause 6: The variant hIL-18 protein of Clause 5, wherein the variant hIL-18 protein further comprises C38S, C68S, C76S, and C127S substitutions.

Clause 7: A variant hIL-18 protein comprising the following amino acid substitutions: Y1W, C38S, M51Y, M60W, C68S, C76S, D110Y, and C127S.

Clause 8: The variant hIL-18 protein of Clause 7 comprising an amino acid sequence as set forth in SEQ ID NO:3.

Clause 9: A variant hIL-18 protein comprising the following amino acid substitutions: Y1K, C38S, M51S, M60W, C68S, C76S, S105E, D110Y, and C127S.

Clause 10: The variant hIL-18 protein of Clause 9 comprising an amino acid sequence as set forth in SEQ ID NO:4.

Clause 11: The variant hIL-18 protein of any one of Clauses 1 to 10, wherein the variant hIL-18 protein exhibits reduced or no detectable binding to IL-18 binding protein as compared to wild-type hIL-18 (SEQ ID NO:2).

Clause 12: The variant hIL-18 protein of any one of Clauses 1 to 11, wherein the variant hIL-18 protein has increased IL-18 activity in the presence of IL-18 binding protein as compared to wild-type hIL-18 (SEQ ID NO:2).

Clause 13: A nucleic acid encoding the variant hIL-18 protein of any one of Clauses 1 to 12.

Clause 14: An expression vector comprising a nucleic acid encoding the variant hIL-18 protein of any one of Clauses 1 to 12.

Clause 15: A host cell comprising the expression vector of Clause 14.

Clause 16: A method of making a variant hIL-18 protein comprising culturing the host cell of Clause 15 under condition wherein the variant hIL-18 protein is expressed, and recovering the variant hIL-18 protein.

Clause 17: A variant human IL-18 (hIL-18) fusion protein comprising a variant hIL-18 protein attached to a human albumin binding domain (ABD), wherein the ABD comprises an antibody heavy chain variable domain (VH), and an antibody light chain variable domain (VL).

Clause 18: The variant hIL-18 fusion protein of Clause 17, wherein the VH comprises an amino acid sequence as set forth in SEQ ID NO:5, and the VL comprises an amino acid sequence as set forth in SEQ ID NO:9.

Clause 19: The variant hIL-18 fusion protein of Clause 17 or 18, wherein the variant hIL-18 protein comprises a substitution at one or more of the following amino acids: Y1, M51, M60, S105, and/or D110, as compared to human wild-type IL-18 (SEQ ID NO:2).

Clause 20: The variant hIL-18 fusion protein of any one of Clauses 17 to 19, wherein the substitution is selected from one or more of the following: Y1W, Y1K, M51Y, M51S, M60W, S105E, and/or D110Y.

Clause 21: The variant hIL-18 fusion protein of Clause 20, wherein the substitutions include: Y1W, M51Y, M60W, and D110Y.

Clause 22: The variant hIL-18 fusion protein of Clause 20, wherein the substitutions include: Y1K, M51S, M60W, S105E, and D110Y.

Clause 23: The variant hIL-18 fusion protein of any one of Clauses 17 to 22, wherein the variant hIL-18 protein further comprises one or more of the following amino acid substitutions: C38S, C68S, C76S, and/or C127S, as compared to human wild-type IL-18 (SEQ ID NO: 2).

Clause 24: The variant hIL-18 fusion protein of Clause 23, wherein the variant hIL-18 protein further comprises C38S, C68S, C76S, and C127S substitutions.

Clause 25: The variant hIL-18 fusion protein of Clause 17 or 18, wherein the variant hIL-18 protein comprises the following amino acid substitutions: Y1W, C38S, M51Y, M60W, C68S, C76S, D110Y, and C127S.

Clause 26: The variant hIL-18 fusion protein of Clause 25, wherein the variant hIL-18 protein comprises an amino acid sequence as set forth in SEQ ID NO:3.

Clause 27: The variant hIL-18 fusion protein of Clause 17 or 18, wherein the variant hIL-18 protein comprises the following amino acid substitutions: Y1K, C38S, M51S, M60W, C68S, C76S, S105E, D110Y, and C127S.

Clause 28: The variant hIL-18 fusion protein of Clause 27, wherein the variant hIL-18 protein comprises an amino acid sequence as set forth in SEQ ID NO:4.

Clause 29: The variant hIL-18 fusion protein of any one of Clauses 17 to 28, wherein the human albumin binding domain is an scFv, and wherein the VH is attached to the VL by an scFv linker.

Clause 30: The variant hIL-18 fusion protein of any one of Clauses 17 to 29, wherein the variant hIL-18 protein is attached to the human albumin binding domain by a peptide linker.

Clause 31: The variant hIL-18 fusion protein of Clause 30, wherein the variant hIL-18 fusion protein comprises from N- to C-terminus: variant hIL-18-peptide linker-ABD.

Clause 32: The variant hIL-18 fusion protein of Clause 30, wherein the variant hIL-18 fusion protein comprises from N- to C-terminus: ABD-peptide linker-variant hIL-18.

Clause 33: The variant hIL-18 fusion protein of any one of Clauses 17 to 32, wherein the variant hIL-18 protein exhibits reduced or no detectable binding to IL-18 binding protein as compared to wild-type hIL-18 (SEQ ID NO:2).

Clause 34: The variant hIL-18 fusion protein of any one of Clauses 17 to 31, wherein the variant hIL-18 protein has increased IL-18 activity in the presence of IL-18 binding protein, as compared to wild-type hIL-18 (SEQ ID NO:2).

Clause 35: A nucleic acid encoding the variant hIL-18 fusion protein of any one of Clauses 17-34.

Clause 36: An expression vector comprising a nucleic acid encoding the variant hIL-18 fusion protein of any one of Clauses 17-34.

Clause 37: A host cell comprising the expression vector of Clause 36.

Clause 38: A method of making a variant hIL-18 fusion protein comprising culturing the host cell of Clause 37 under condition wherein the variant hIL-18 fusion protein is expressed, and recovering the variant hIL-18 fusion protein.

Clause 39: An IL-18/IL-12 albumin binding domain fusion protein comprising: a) a human IL-18 (hIL-18); b) a human IL-12 (hIL-12); and c) a human albumin binding domain (hABD), Wherein the human albumin binding domain is an scFv that comprises an antibody heavy chain variable domain (VH), an antibody light chain variable domain (VL), and an scFv linker that attaches the VH to the VL, and wherein the hIL-18 is attached to the human albumin binding domain by a first peptide linker, and the hIL-12 is attached to the human albumin binding domain by a second peptide linker.

Clause 40: The IL-18/IL-12 albumin binding domain fusion protein of Clause 39, wherein the IL-18/IL-12 albumin binding domain fusion protein comprises from N- to C-terminus: hIL-18-linker 1-hABD-linker 2-hIL-12.

Clause 41: The IL-18/IL-12 albumin binding domain fusion protein of Clause 39, wherein the IL-18/IL-12 albumin binding domain fusion protein comprises from N- to C-terminus: hIL-12-linker 2-hABD-linker 1-hIL18.

Clause 42: The IL-18/IL-12 albumin binding domain fusion protein of any one of Clauses 39 to 42, wherein the VH comprises an amino acid sequence as set forth in SEQ ID NO:5, and the VL comprises an amino acid sequence as set forth in SEQ ID NO:9.

Clause 43: The IL-18/IL-12 albumin binding domain fusion protein of any one of Clauses 39 to 42, wherein the hIL-18 protein is a variant hIL-18 protein that comprises a substitution at one or more of the following amino acid positions: Y1, M51, M60, S105, and/or D110, as compared to human wild-type IL-18 (SEQ ID NO:2).

Clause 44: The IL-18/IL-12 albumin binding domain fusion protein of Clause 43, wherein the substitution is selected from one or more of the following: Y1W, Y1K, M51Y, M51S, M60W, S105E, and/or D110Y.

Clause 45: The IL-18/IL-12 albumin binding domain fusion protein of Clause 44, wherein the substitutions include: Y1W, M51Y, M60W, and D110Y.

Clause 46: The IL-18/IL-12 albumin binding domain fusion protein of Clause 44, wherein the variant hIL-18 protein comprises the following substitutions: Y1K, M51S, M60W, S105E, and D110Y.

Clause 47: The IL-18/IL-12 albumin binding domain fusion protein of any one of Clauses 43 to 46, wherein the variant hIL-18 protein further comprises one or more of the following amino acid substitutions: C38S, C68S, C76S, and/or C127S, as compared to wild-type hIL-18 (SEQ ID NO:2).

Clause 48: The IL-18/IL-12 albumin binding domain fusion protein of Clause 47, wherein the variant hIL-18 protein further comprises C38S, C68S, C76S, and C127S substitutions.

Clause 49: The IL-18/IL-12 albumin binding domain fusion protein of Clause 43, wherein the variant hIL-18 protein comprises the following amino acid substitutions: Y1W, C38S, M51Y, M60W, C68S, C76S, D110Y, and C127S.

Clause 50: The IL-18/IL-12 albumin binding domain fusion protein of Clause 49, wherein the variant hIL-18 protein has an amino acid sequence as set forth in SEQ ID NO:3

Clause 51: The IL-18/IL-12 albumin binding domain fusion protein of Clause 43, wherein the variant hIL-18 protein comprises the following amino acid substitutions: Y1K, C38S, M51S, M60W, C68S, C76S, S105E, D110Y, and C127S.

Clause 52: The IL-18/IL-12 albumin binding domain fusion protein of Clause 51, wherein the variant hIL-18 protein has an amino acid sequence as set forth in SEQ ID NO:4.

Clause 53: The IL-18/IL-12 albumin binding domain fusion protein of any one of Clauses 39 to 52, wherein the hIL-12 protein has an amino acid sequence as set forth in SEQ ID NO: 14.

Clause 54: The IL-18/IL-12 albumin binding domain fusion protein of any one of Clauses 43 to 53, wherein the variant hIL-18 protein exhibits reduced or no detectable binding to IL-18 binding protein as compared to wild-type hIL-18 (SEQ ID NO:2).

Clause 55: The IL-18/IL-12 albumin binding domain fusion protein of any one of Clauses 43 to 54, wherein the variant hIL-18 protein has increased IL-18 activity in the presence of IL-18 binding protein, as compared to wild-type hIL-18 (SEQ ID NO:2).

Clause 56: A nucleic acid encoding the IL-18/IL-12 albumin binding domain fusion protein of any one of Clauses 39-55.

Clause 57: An expression vector comprising a nucleic acid encoding the IL-18/IL-12 albumin binding domain fusion protein of any one of Clauses 39-56.

Clause 58: A host cell comprising the expression vector of Clause 57.

Clause 59: A method of making an IL-18/IL-12 albumin binding domain fusion protein comprising culturing the host cell of Clause 58 under condition wherein the IL-18/IL-12 albumin binding domain fusion protein is expressed, and recovering the IL-18/IL-12 albumin binding domain fusion protein.

EXAMPLES

The examples herein are provided to illustrate advantages and benefits described herein and to further assist a person of ordinary skill in the art with making and using the IL-18 variants described herein. The examples herein are also presented in order to more fully illustrate the aspects described herein. The examples should in no way be construed as limiting the scope described herein, as defined by the appended claims. The examples can include or incorporate any of the variations, aspects, or embodiments described herein described above. The variations, aspects or embodiments described above may also further each include or incorporate the variations of any or all other variations, aspects or embodiments described herein.

Example 1: IL-18/IL-12 Albumin Binding Domain Fusion Protein Engineering and Activity Assessment Several IL-18/IL-12 albumin binding domain fusion proteins were made and assessed for IL-18 activity as summarized below.

TABLE 2

IL-18/IL-12 Albumin Binding Domain Fusion Proteins

| Fusion Protein | Human IL-18 variant | Albumin binding domain | IL-12 |
|---|---|---|---|
| hIL18-ABD-hIL12-Variant A | Y1W, C38S, M51Y, M60W, C68S, C76S, D110Y, C127S (SEQ ID NO: 3) | A10m3 (SEQ ID NO: 13) | Human IL-12 single chain (SEQ ID NO: 14) |
| hIL18-ABD-hIL12-Variant B | Y1K, C38S, M51S, M60W, C68S, C76S, S105E, D110Y, C127S (SEQ ID NO: 4) | A10m3 (SEQ ID NO: 13) | Human IL-12 single chain (SEQ ID NO: 14) |
| hIL18(Cys to Ser)-ABD-hIL12 | C38S, C68S, C76S, C127S | A10m3 (SEQ ID NO: 13) | Human IL-12 single chain (SEQ ID NO: 14) |

The IL-18/IL-12 albumin binding domain fusion proteins each included a variant of a human IL-18. Two of the variant IL-18 proteins ("variant A" (SEQ ID NO: 3) and IL-18 "variant B" (SEQ ID NO: 4, FIG. 1) were modified to reduce binding to IL-18 binding protein while retaining IL-18 activity. Amino acid modifications were based on a compilation of literature review, 3D X-ray crystallography structures, and computer modeling analysis. IL-18 Variant A and B further included cysteine/serine amino acid substitutions to reduce IL-18 aggregation. A third variant IL-18 was engineered to only include the cysteine/serine amino acid substitutions. Each of the IL-18/IL-12 ABD fusion proteins further included an albumin binding domain (SEQ ID NO: 13, FIG. 2), and a single chain human IL-12 (SEQ ID NO: 14, FIG. 3).

The IL-18/IL-12 albumin binding domain fusion proteins (termed, "hIL18-ABD-hIL12 Variant A," "hIL18-ABD-hIL12 Variant B," and "hIL18 (Cys to Ser)-ABD-hIL12") were tested for IL-18 activity in the absence of inhibitory IL-18 binding protein using a HEK-Blue™ IL-18 Reporter Assay (Invivogen). Recombinant hIL-18, and hIL-12 were also tested for IL-18 activity.

As shown in FIG. 7, all three of the IL-18/IL-12 ABD fusion proteins exhibited increased IL-18 functional activity based on IL-18 HEK-Blue™ Assay. As expected, recombinant hIL-12 control induced no functional IL-18 activity. The hIL18-ABD-hIL12 Variant B displayed an $EC_{50}$ value of 17 pM. The hIL18-ABD-hIL12 Variant A exhibited an $EC_{50}$ value of 1.9 pM. The recombinant hIL-18 reference control exhibited an $EC_{50}$ value of 0.53 PM, and the hIL18 (Cys to Ser)-ABD-hIL12 showed an $EC_{50}$ value of 0.17 pM. In summary, the IL-18 bioactivity of Variant A showed approximately 9-fold better activity than Variant B.

Example 2: IL-18/IL-12 Albumin Binding Domain Fusion Protein Orthogonal Activity Assessment The IL-18/IL-12 albumin binding domain fusion proteins (hIL18-ABD-hIL12-Variant A, and hIL18-ABD-hIL12—Variant B) were tested for IL-18 activity using the IL-18 Effector Bright-Glo™ Luciferase Assay System (Promega). A recombinant hIL-18 reference control was also tested. As shown in FIGS. 8A-C, all molecules tested exhibited IL-18 activity. The hIL18-ABD-hIL12 Variant B exhibited an $EC_{50}$ value of 125 pM, and the hIL18-ABD-hIL12 Variant A showed an $EC_{50}$ value of 3.4 pM. The recombinant hIL-18 reference control exhibited an $EC_{50}$ value of 0.33 pM. The values produced by the Bright-Glo™ Luciferase Assay compare similarly to those produced by the HEK-Blue™ Assay in Example 1.

Example 3: IL-18 Receptor Binding Activity of IL-18 Variant A and B

The hIL-18 Variants were tested for IL-18 activity in the absence (FIG. 9A; Variant A only) and presence (FIG. 9B—Variant A; and FIG. 9C—Variant B) of IL-18BP using a HEK-Blue™ IL-18 Reporter Assay (Invivogen). Recombinant hIL-18 (NIBSC wildtype) was also tested for IL-18 receptor activation.

Briefly, HEK Blue™ IL-18 cells were harvested, and 50 µL was added to an initial assay plate at a density of 0.35×10⁶ cells/mL. hIL18 Variant A was prepared at varying concentrations (100 ng/mL to 0.00001 ng/mL), added to the initial assay plate, and incubated for 20±2 hours at 37±1° C. with 5±1% $CO_2$. Then, 50 µL of the cell suspension solution was mixed with 150 µL of QUANTI-Blue™ solution in a final assay plate. The reactions were incubated for 45±15 minutes at 37±1° C. with 5±1% $CO_2$. Each plate was then measured for absorbance at 640 nm. As shown in FIG. 9A, hIL-18 Variant A retains IL-18 receptor binding activity comparable to wild-type IL-18.

Figure 9B:
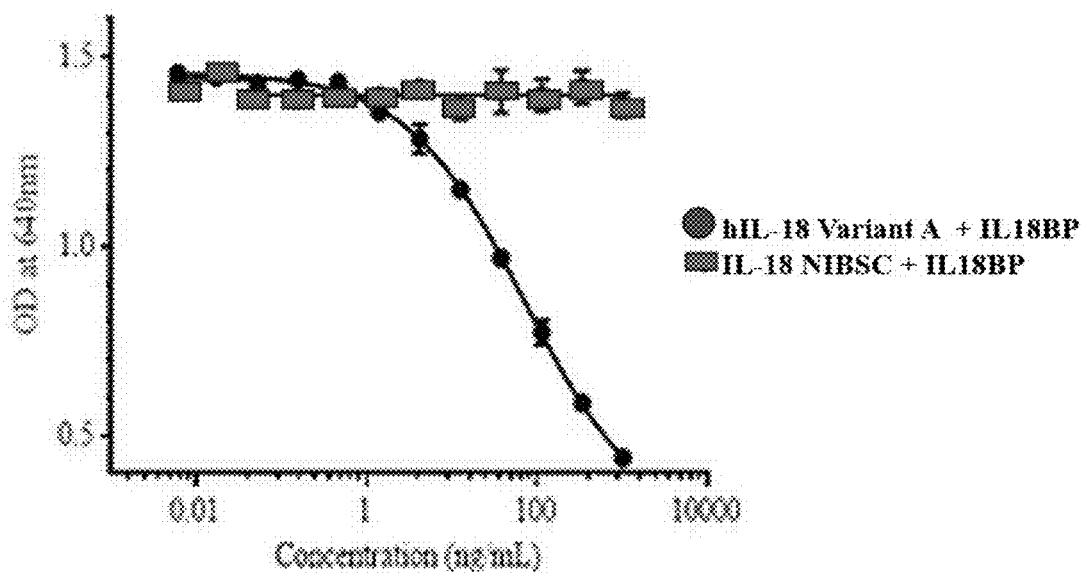
Figure 11:
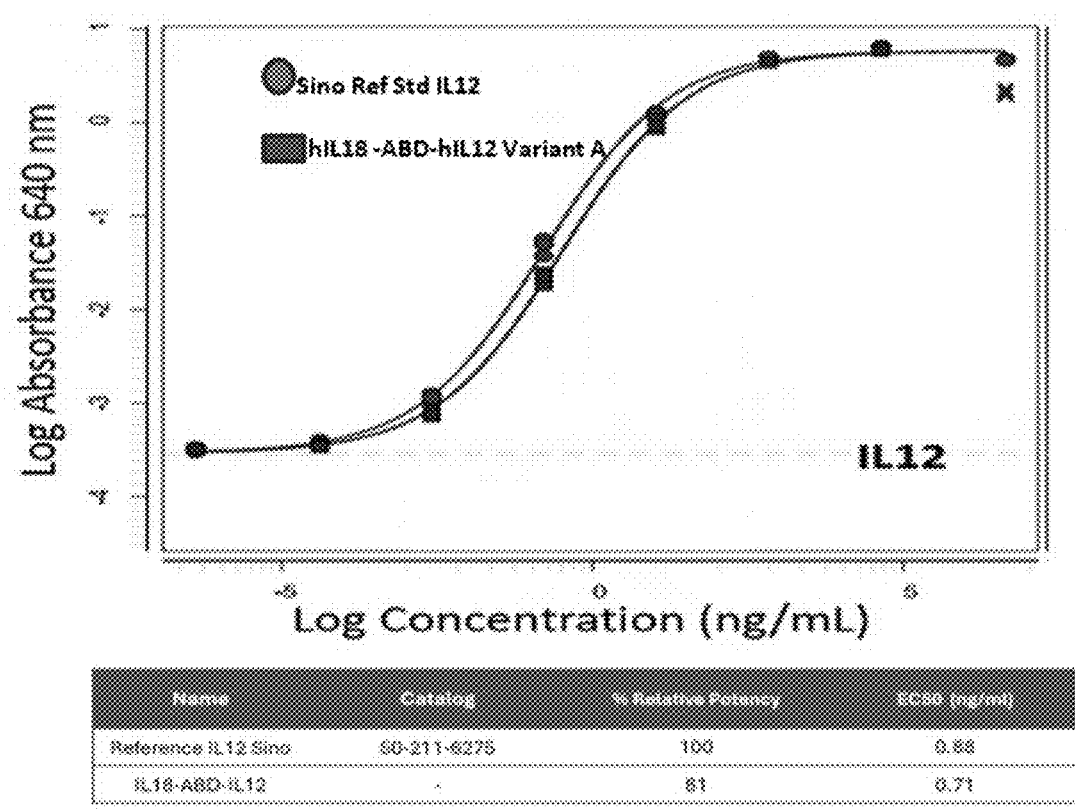
FIG. 11 depicts a summary of a study to assess the IL-12 activity of an exemplary IL-18-ABD-IL12 Variant A construct.

IL-18BP inhibition was assessed for both Variant A and B using HEK Blue™ IL-18 cells. Briefly, 50 µL of IL-18BP at varying concentrations (23.8 nM to 0.00013 nM) were prepared and mixed with 50 µL of hIL18 Variant A protein at 0.124 nM in an initial assay plate. The solutions were incubated for one hour at 37±1° C. with 5±1% $CO_2$. Then, 50 µL of harvested HEK Blue™ IL-18 cells at a density of 0.35×10⁶ cells/mL were added to the initial assay plate and incubated at 37±1° C. with 5=1% $CO_2$ for 20±2 hours. Then, 50 µL of the cell suspension solution was mixed with 150 µL of QUANTI-Blue™ solution in a final assay plate. The reactions were incubated for one hour at 37±1° C. with 5±1% $CO_2$, and then measured for absorbance at 640 nm. As shown in FIG. 9B, hIL-18 Variant A exhibited no detectable binding to inhibitory IL-18BP, whereas wild-type hIL-18 bound to IL-18BP in a dose-dependent manner. Similarly, hIL-18 Variant B exhibited no detectable binding to inhibitory IL-18BP, whereas wild-type hIL-18 bound to IL-18BP in a dose-dependent manner as shown in FIG. 9C. In summary, both Variant A and B showed no loss of bioactivity when incubated with the inhibitor IL-18BP, thus demonstrating no detectable interaction between the hIL-18 variants to IL-18BP. These data demonstrate the potency of IL-18 fusion proteins with hIL-18 Variant A and B in the presence of IL-18BP.

Example 4. Detection of Binding Affinity and Kinetics of IL18-ABD-IL12 Variant A to IL-18BP The hIL18-ABD-IL12 Variant A molecule and a reference hIL-18 control molecule were tested for binding activity to IL-18BP by Biacore™ SPR Assay. Briefly, a Biacore™ T200 instrument was used with a CM5 sensor chip. IL-18BP was the immobilized ligand. The assay was performed using a buffer comprising 10 mM HEPES pH 7.4, 150 mM NaCl, 3 mM EDTA, 0.05% Tween 20. The capture for hIL18-ABD-hIL12 Variant A was 19 seconds at 10 μL/min, and the capture for the reference IL-18 control was 45 seconds at 10 μL/min. Each molecule was injected in a separate cycle for 90 seconds at a flow rate of 30 μL per minute, and the complex was allowed to dissociate for 600 seconds. The surface was regenerated by injecting two pulses of 3 M magnesium chloride for 20 seconds each. The assay was performed at 25° C.

A concentration-dependent signal was observed upon titration of the reference hIL-18 control molecule with a $K_D$ of 56 pM (FIG. 10A). However, no detectable binding was observed for the hIL18-ABD-hIL12 Variant A molecule to IL-18BP (FIG. 10B). Additionally, the bifunctional hIL18-ABD-hIL12 molecule maintained both IL-18 and IL-12 bioactivity, suggesting no significant steric hindrance (FIG. 11).

Specific embodiments provided herein can be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments so claimed are inherently or expressly described and enabled herein.

In cases where numerical values are indicated herein, the skilled person will understand that the technical effect of the feature in question is ensured within an interval of accuracy, which typically encompasses a deviation of the numerical value given of +10% or of +5%. At the very least, and not as an attempt to limit the application of the doctrine of equivalents to the scope of the claims, each numerical parameter should at least be construed considering the number of reported significant digits and by applying ordinary rounding techniques.

Unless otherwise indicated, all numbers expressing quantities of ingredients, properties such as molecular weight and median size, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained.

The terms "a," "an," "the" and similar referents used in the context of the description herein (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples or exemplary language (e.g., "such as") provided herein is intended merely to better illuminate the specification and does not pose a limitation on the scope of the claims. No language in the specification should be construed as indicating any non-claimed element essential to the practice of the disclosure.

Unless specifically stated or obvious from context, as used herein, the term "or" is understood to be inclusive and covers both "or" and "and."

Groupings of alternative elements or embodiments provided herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments are described herein, including the best mode known for carrying out methods provided herein. Of course, variations on these described embodiments will become apparent upon reading the foregoing description. One can be expected to employ such variations as appropriate and can be practiced other than as specifically described herein. Accordingly, this description includes all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context.

It is to be understood that the embodiments provided herein are illustrative of the principles of the description herein. Other modifications that can be employed are within the scope of the description. Thus, by way of example, but not of limitation, alternative configurations can be utilized in accordance with the teachings herein. Accordingly, the presented information is not limited to that precisely as shown and described.

While the present description has been described and illustrated herein by references to various specific materials, procedures, and examples, it is understood that the description is not restricted to the particular combinations of materials and procedures selected for that purpose. Numerous variations of such details can be implied as will be appreciated. It is intended that the specification and examples be considered as exemplary only, with the true scope and spirit of the specification being indicated by the following claims. All references, patents, and patent applications referred to in this application are herein incorporated by reference in their entirety.

Unless defined otherwise, all technical and scientific terms used herein have the same meaning as commonly understood. Although other probes, compositions, methods, and kits similar, or equivalent, to those described herein can be used in the practice described herein, the materials and methods are described herein. It is to be understood that the terminology used herein is for the purpose of describing embodiments only and is not intended to be limiting.

Unless specifically stated or obvious from context, as used herein, the term "about" is understood as within a range of normal tolerance, for example within 2 standard deviations of the mean. About is understood to be within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

A stated range is understood to be any value between and at the limits of the stated range. As examples, a range between 1 and 5 includes 1, 2, 3, 4, and 5; a range between 1 and 10 includes 1, 2, 3, 4, 5, 6, 7, 8, 9, and 10; and a range between 1 and 100 includes 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100.

Any aspect or embodiment described herein can be combined with any other aspect or embodiment as described herein.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

What is claimed is:

1. An IL-18/IL-12 albumin binding domain fusion protein comprising:

a) a human IL-18 (hIL-18), wherein the hIL-18 protein is a variant hIL-18 protein that comprises a substitution at one or more of the following amino acid positions: Y1, M51, M60, S105, and/or D110, relative to human wild-type IL-18 (SEQ ID NO:2);

b) a human IL-12 (hIL-12); and c) a human albumin binding domain (hABD), wherein the human albumin binding domain is an scFv that comprises an antibody heavy chain variable domain (VH), an antibody light chain variable domain (VL), and an scFv linker that attaches the VH to the VL, wherein the VH comprises an amino acid sequence as set forth in SEQ ID NO:5, and the VL comprises an amino acid sequence as set forth in SEQ ID NO:9, and wherein the hIL-18 is attached to the human albumin binding domain by a first peptide linker, and the hIL-12 is attached to the human albumin binding domain by a second peptide linker.

2. The IL-18/IL-12 albumin binding domain fusion protein of claim 1, wherein the IL-18/IL-12 albumin binding domain fusion protein comprises from N- to C-terminus: hIL-18-linker 1-hABD-linker 2-hIL-12.

3. The IL-18/IL-12 albumin binding domain fusion protein of claim 1, wherein the IL-18/IL-12 albumin binding domain fusion protein comprises from N- to C-terminus: hIL-12-linker 2-hABD-linker 1-hIL18.

4. The IL-18/IL-12 albumin binding domain fusion protein of claim 1, wherein the substitution is selected from one or more of the following: Y1W, Y1K, M51Y, M51S, M60W, S105E, and/or D110Y.

5. The IL-18/IL-12 albumin binding domain fusion protein of claim 4, wherein the substitutions include: Y1W, M51Y, M60W, and D110Y.

6. The IL-18/IL-12 albumin binding domain fusion protein of claim 4, wherein the variant hIL-18 protein comprises the following substitutions: Y1K, M51S, M60W, S105E, and D110Y.

7. The IL-18/IL-12 albumin binding domain fusion protein of claim 4, wherein the variant hIL-18 protein further comprises one or more of the following amino acid substitutions: C38S, C68S, C76S, and/or C127S relative to wild-type hIL-18 (SEQ ID NO:2).

8. The IL-18/IL-12 albumin binding domain fusion protein of claim 7, wherein the variant hIL-18 protein further comprises C38S, C68S, C76S, and C127S substitutions.

9. The IL-18/IL-12 albumin binding domain fusion protein of claim 8, wherein the variant hIL-18 protein comprises the following amino acid substitutions: Y1W, C38S, M51Y, M60W, C68S, C76S, D110Y, and C127S.

10. The IL-18/IL-12 albumin binding domain fusion protein of claim 9, wherein the variant hIL-18 protein has an amino acid sequence as set forth in SEQ ID NO:3.

11. The IL-18/IL-12 albumin binding domain fusion protein of claim 8, wherein the variant hIL-18 protein comprises the following amino acid substitutions: Y1K, C38S, M51S, M60W, C68S, C76S, S105E, D110Y, and C127S.

12. The IL-18/IL-12 albumin binding domain fusion protein of claim 11, wherein the variant hIL-18 protein has an amino acid sequence as set forth in SEQ ID NO:4.

13. The IL-18/IL-12 albumin binding domain fusion protein of claim 1, wherein the hIL-12 protein has an amino acid sequence as set forth in SEQ ID NO:14.

14. The IL-18/IL-12 albumin binding domain fusion protein of claim 1, wherein the variant hIL-18 protein exhibits no detectable binding to IL-18 binding protein as compared to wild-type hIL-18 (SEQ ID NO:2).

15. A nucleic acid encoding the IL-18/IL-12 albumin binding domain fusion protein of claim 1.

16. An expression vector comprising the nucleic acid of claim 15.

17. A host cell comprising the expression vector of claim 16.

18. A method of making an IL-18/IL-12 albumin binding domain fusion protein comprising culturing the host cell of claim 17 under conditions wherein the IL-18/IL-12 albumin binding domain fusion protein is expressed, and recovering the IL-18/IL-12 albumin binding domain fusion protein.

* * * * *